United States Patent
Cichocki, Jr. et al.

(10) Patent No.: US 11,129,968 B2
(45) Date of Patent: Sep. 28, 2021

(54) METHODS OF MAKING AND IMPLANTING BARBED MICROCATHETERS HAVING FLUID EGRESS OPENINGS FOR INFUSING THERAPEUTIC FLUIDS

(71) Applicant: Ethicon, Inc., Somerville, NJ (US)

(72) Inventors: Frank Richard Cichocki, Jr., Easton, PA (US); Scott Ciarrocca, Stockton, NJ (US)

(73) Assignee: Ethicon, Inc., Somerville, NJ (US)

( * ) Notice: Subject to any disclaimer, the term of this patent is extended or adjusted under 35 U.S.C. 154(b) by 152 days.

(21) Appl. No.: 16/570,028

(22) Filed: Sep. 13, 2019

(65) Prior Publication Data

US 2021/0077781 A1    Mar. 18, 2021

(51) Int. Cl.
*A61M 25/02* (2006.01)
*A61M 25/00* (2006.01)
(Continued)

(52) U.S. Cl.
CPC ........ *A61M 25/02* (2013.01); *A61M 25/0009* (2013.01); *A61M 25/0012* (2013.01);
(Continued)

(58) Field of Classification Search
CPC ...... A61M 25/0015; A61M 2025/0042; A61M 2025/0057; A61M 2025/006; A61M 25/04; A61M 25/02; A61M 25/0084; A61M 25/0043; A61M 25/0009; A61M 25/0012; A61M 2025/0056; A61M 2025/0286; A61M 2025/0089; A61M 25/007; A61F 2/848; A61F 2002/8483; B26F 1/24; B26F 1/18; B26F 1/34; B26F 1/00; B29D 23/00; B29C 2793/0036; B29C 2793/0027; B29C 2793/0045
(Continued)

(56) References Cited

U.S. PATENT DOCUMENTS 4,307,723 A * 12/1981 Finney ................. A61F 2/04
604/544
5,052,998 A * 10/1991 Zimmon ............... A61M 25/04
604/8

(Continued)

FOREIGN PATENT DOCUMENTS

EP    2759266    7/2014
EP    3202336    8/2017

*Primary Examiner* — Jeffrey M Wollschlager

(57) ABSTRACT

A method of making a barbed microcatheter having fluid egress openings includes obtaining a barbed microcatheter blank having a hollow tube with a proximal end, a distal end, and an elongated lumen that extends between the proximal and distal ends of the hollow tube, and first and second flattened regions that extend along opposite sides of the hollow tube. The method includes removing material from the first and second flattened regions of the barbed microcatheter blank to form barbs projecting outwardly from the opposite sides of the hollow tube, and using cutting elements for forming fluid egress openings in a wall of the hollow tube that are in fluid communication with the elongated lumen of the hollow tube. The method includes forming a tissue anchor that is connected with the proximal end of the hollow tube, and securing a surgical needle with the distal end of the hollow tube.

16 Claims, 25 Drawing Sheets

(51) Int. Cl.
*B29D 23/00* (2006.01)
*B26F 1/18* (2006.01)
*B26F 1/34* (2006.01)
*B26F 1/00* (2006.01)
*B26F 1/24* (2006.01)
*A61M 25/04* (2006.01)

(52) U.S. Cl.
CPC .... *A61M 25/0015* (2013.01); *A61M 25/0084* (2013.01); *B26F 1/00* (2013.01); *B26F 1/18* (2013.01); *B26F 1/24* (2013.01); *B26F 1/34* (2013.01); *B29D 23/00* (2013.01); *A61M 25/04* (2013.01); *A61M 2025/0056* (2013.01); *A61M 2025/0057* (2013.01); *A61M 2025/0089* (2013.01); *A61M 2025/0286* (2013.01); *B29C 2793/0027* (2013.01); *B29C 2793/0036* (2013.01); *B29C 2793/0045* (2013.01)

(58) Field of Classification Search
USPC .................................................. 264/138–163
See application file for complete search history.

(56) References Cited

U.S. PATENT DOCUMENTS

| | | | |
|---|---|---|---|
| 5,129,910 A * | 7/1992 | Phan | A61B 17/22031 604/264 |
| 5,458,582 A | 10/1995 | Nakeo | |
| 5,957,901 A * | 9/1999 | Mottola | A61M 25/007 604/264 |
| 5,984,965 A * | 11/1999 | Knapp | A61F 2/04 623/23.7 |
| 6,589,213 B2 | 7/2003 | Reydel | A61M 25/0043 600/585 |
| 6,848,152 B2 * | 2/2005 | Genova | B21J 5/068 29/7.1 |
| 7,225,512 B2 * | 6/2007 | Genova | B26D 3/08 29/7.1 |
| 7,704,230 B2 | 4/2010 | Chatlynne et al. | |
| 7,875,055 B2 | 1/2011 | Cichocki | |
| 8,100,941 B2 | 1/2012 | Lindh et al. | |
| 8,128,656 B2 | 3/2012 | Cichocki | |
| 8,226,684 B2 | 7/2012 | Nawrocki et al. | |
| 8,257,393 B2 | 9/2012 | Cichocki, Jr. | |
| 8,348,973 B2 | 1/2013 | Stopek et al. | |
| 8,443,506 B2 * | 5/2013 | Maiorino | A61B 17/06166 29/458 |
| 8,603,185 B2 * | 12/2013 | Shah | A61M 27/008 623/23.64 |
| 8,641,732 B1 * | 2/2014 | Goraltchouk | A61B 17/06166 606/228 |
| 8,747,436 B2 * | 6/2014 | Nawrocki | A61B 17/06166 606/228 |
| 8,795,332 B2 * | 8/2014 | Leung | A61B 17/04 606/228 |
| 8,821,539 B2 | 9/2014 | Rousseau | |
| 9,011,133 B2 * | 4/2015 | Marczyk | A61B 17/06166 425/295 |
| 9,237,889 B2 | 1/2016 | Dumanian et al. | |
| 9,592,362 B2 | 3/2017 | Chen et al. | |
| 9,597,426 B2 | 3/2017 | Ostapoff et al. | |
| 9,687,227 B2 * | 6/2017 | Marczyk | A61B 17/06166 |
| 9,775,928 B2 | 10/2017 | Ostapoff et al. | |
| 9,868,238 B1 * | 1/2018 | Scopton | B29B 13/024 |
| 9,884,165 B2 * | 2/2018 | Patterson | A61M 25/0032 |
| 2003/0149447 A1 * | 8/2003 | Morency | A61B 17/06166 606/228 |
| 2007/0257395 A1 * | 11/2007 | Lindh | A61B 17/06166 264/171.12 |
| 2008/0269686 A1 * | 10/2008 | Young | A61J 15/0069 604/174 |
| 2010/0160961 A1 | 6/2010 | Nawrocki et al. | |
| 2011/0251640 A1 * | 10/2011 | Lauria | A61B 17/06166 606/228 |
| 2011/0288583 A1 * | 11/2011 | Goraltchouk | A61B 17/08 606/228 |
| 2013/0261605 A1 * | 10/2013 | Gregersen | A61M 25/0023 604/523 |
| 2014/0222071 A1 | 8/2014 | Perkins et al. | |
| 2017/0224338 A1 * | 8/2017 | Sung | A61B 17/06166 |

* cited by examiner

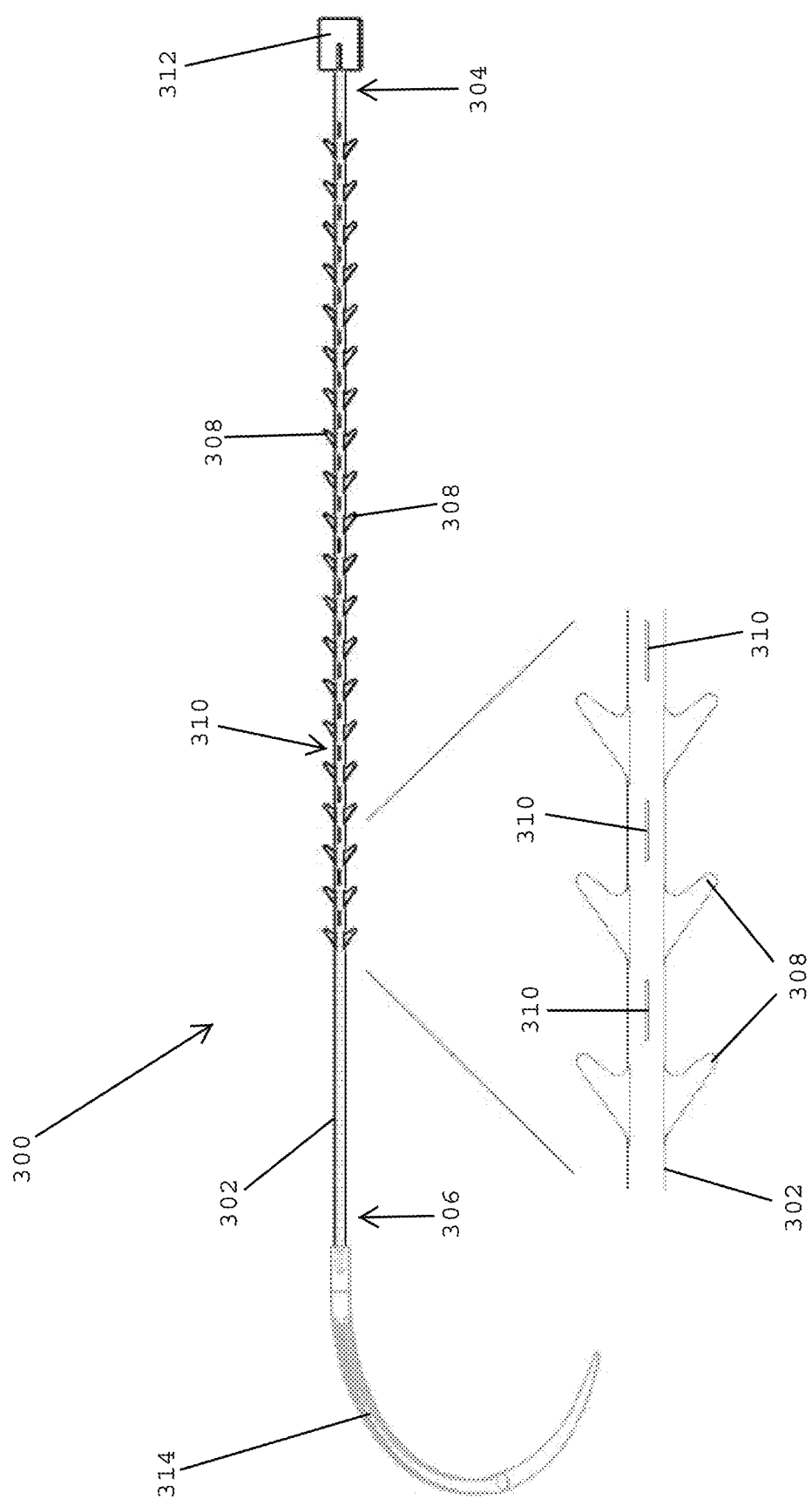

METHODS OF MAKING AND IMPLANTING BARBED MICROCATHETERS HAVING FLUID EGRESS OPENINGS FOR INFUSING THERAPEUTIC FLUIDS

CROSS-REFERENCE TO RELATED APPLICATIONS

The present patent application is related to commonly assigned U.S. patent application Ser. No. 16/570,017, filed on Sep. 13, 2019, the disclosure of which is hereby incorporated by reference herein.

BACKGROUND OF THE INVENTION

Field of the Invention

The present patent application is generally related to medical devices, and is more specifically related to catheters that are implanted in patients.

Description of the Related Art

Many medical treatment protocols involve infusing therapeutic fluids into selected areas of a patient's body. The types of therapeutic fluids that are typically employed by physicians for treating patients include anesthetics, antibiotics, antimicrobial agents, chemotherapy agents, and growth factors.

Historically, therapeutic fluids have been delivered to patients using catheters that are temporarily implanted in the patients for delivering the therapeutic fluids during a treatment period. At the end of the treatment period, the catheters are removed from the patients. Unfortunately, catheter removal often results in wound disruption and pain for the patients.

In many instances, linear catheters are used for treating patients. Linear catheters are typically held in place using sutures or other fixation devices (e.g., staples), which can complicate the surgery, introduce additional foreign bodies into the patient, and compromise catheter performance by obstructing the flow of therapeutic fluids through the catheter.

In some instances, rather than using a linear catheter, it is necessary to use a non-linear catheter that is arranged in a complex three-dimensional configuration inside the patient. For example, a non-linear catheter having a three-dimensional configuration may be used to extend around an object located inside the body, such as a tumor, an artificial joint, or a complex surgical wound. Due to their non-linear shape, medical personnel often have great difficulty removing non-linear catheters from patients.

Catheters that are implanted in patients come in many different sizes. In some instances, medical personnel are required to use fine catheters, also referred to as microcatheters, for delivering therapeutic fluids to patients. Creating fluid passageways in fine catheters can be extremely challenging due to the exact tolerances that are required in order to maintain uniform fluid flow over the lengths of the fine catheter.

When forming fluid passageways in larger sized catheters, sharpened hollow stainless steel tubes may be used to core punch material from the wall of the catheter. This approach becomes more challenging as the size of the catheter decreases, because there is a limit to the size of the sharpened hollow stainless steel tubing that may be used for making the fluid passageways in the catheters. Even if exceptionally fine steel tubing can be procured for making the fluid passages, the material that is core punched from the wall of the catheter to form the fluid passages tends to become lodged inside the lumen of the catheter and must be removed from the lumen. Removing the punched material carries its own set of challenges.

Fluid passages can be formed in catheter tubes using lasers for forming the passages. It is difficult to precisely control the power levels of a laser, however, so that lasers formed fluid passages are often drilled all the way through the catheter tubing as opposed to remaining on only one side of the catheter tube. Lasers also vaporize and ablate material, which can re-condense on the catheter tube or inside the catheter tube. Moreover, the chemical structure of the ablated/vaporized material is often changed by the intense heat of the laser so that the laser-drilled catheter will no longer be biocompatible or easily quantified for the purposes of design control and regulatory registration of medical devices. In addition, lasers tend to locally heat material and change the structure and molecular orientation of the catheter tube material, which results in catheters having inferior mechanical properties. Finally, lasers providing sufficient power and spot sizes of less than 30 um can be quite expensive, which will increase manufacturing costs.

In view of the above-noted deficiencies, there remains a need for systems, devices and methods for safely, effectively, economically, and reliably mass-producing microcatheters having fluid egress openings.

There also remains a need for systems, devices and methods for manufacturing microcatheters having fluid egress openings that have different sizes along the length of the microcatheter in order to achieve uniform fluid delivery.

Moreover, there remains a need for microcatheters having fluid egress openings having different sizes including smaller fluid egress openings located closer to a fluid source and larger fluid egress openings located further away from the fluid source.

In addition, there remains a need for systems, devices and methods for making microcatheters with fluid egress openings without altering the molecular structure, properties, and/or chemistry of the materials used to make the microcatheter.

Furthermore, there remains a need for automated systems and methods of safely, effectively, economically, and reliably mass-producing microcatheters that have fine fluid egress openings for locally delivering therapeutic fluids to patients.

There also remains a need for absorbable, barbed microcatheters having fluid egress openings for delivering therapeutic fluids to patients, whereby the microcatheters are absorbable by the patients' bodies and do not need to be removed from the patients.

SUMMARY OF THE INVENTION

In one embodiment, a microcatheter having fluid egress openings for delivering therapeutic fluids to a patient is made from bioabsorbable materials, which obviates the need for catheter removal at the end of a treatment period.

In one embodiment, a microcatheter having fluid egress openings for delivering therapeutic fluids incorporates a continuous fixation method, such as barbs, which allows medical personnel (e.g., a surgeon) to precisely place the microcatheter inside a patient without requiring additional fixation mechanisms such as sutures or staples. Such a catheter (e.g., a barbed microcatheter) may be easily placed pen-operatively in any configuration desired with relative ease and with minimal additional procedure time.

In one embodiment, a microcatheter having fluid egress openings for delivering therapeutic fluids preferably includes an elongated, central lumen that extends along the length of the catheter. The microcatheter preferably includes punched or cut fixation barbs for holding the catheter in place inside a patient.

In one embodiment, a barbed microcatheter for delivering fluids to a patient preferably includes a hollow tube having a proximal end, a distal end, and an elongated lumen that extends between the proximal and distal ends of the hollow tube, barbs projecting outwardly from the hollow tube, and a plurality of fluid egress openings formed in the hollow tube that are in fluid communication with the elongated lumen of the hollow tube.

In one embodiment, the fluid egress openings are spaced from one another between the proximal and distal ends of the hollow tube.

In one embodiment, the fluid egress openings may be evenly spaced from one another between the proximal and distal ends of the hollow tube.

In one embodiment, each of the fluid egress openings may be the same size.

In one embodiment, two or more of the fluid egress openings may have different sizes. In one embodiment, the sizes of the fluid egress openings may increase progressively in size between an end of the hollow tube that is closer to a fluid source and an end of the hollow tube that is further away from the fluid source.

In one embodiment, the fluid egress openings are round holes.

In one embodiment, the fluid egress openings are elongated slits. In one embodiment, the hollow tube has a longitudinal axis that extends between the proximal and distal ends of the hollow tube, and the elongated slits have lengths that extend along a common axis that is parallel with the longitudinal axis of the hollow tube.

In one embodiment, the hollow tube preferably has an outer surface and an inner surface that surrounds the elongated lumen. In one embodiment, the fluid egress openings are formed in the hollow tube and extend from the outer surface of the hollow tube to the inner surface of the hollow tube for being in fluid communication with the elongated lumen.

In one embodiment, the inner surface of the hollow tube preferably defines an inner cross-sectional diameter of the hollow tube and the outer surface of the cylindrical wall preferably defines an outer cross-sectional diameter of the hollow tube that is about 2× larger than the inner cross-sectional diameter of the hollow tube.

In one embodiment, the hollow tube has a wall thickness of about 0.125 mm, the outer cross-sectional diameter of the hollow tube is about 0.50 mm and the inner cross-sectional diameter of the hollow tube is about 0.25 mm.

In one embodiment, the barbed microcatheter is desirably made of an absorbable, biocompatible polymer so that the barbed microcatheter will absorb and will not have to be removed from the patient at the end of a therapy period.

In one embodiment, a barbed microcatheter for delivering fluids to tissue desirably includes a hollow tube having a proximal end, a distal end, and an elongated lumen disposed inside the hollow tube that extends between the proximal and distal ends of the hollow tube, barbs projecting outwardly from an outer surface the hollow tube, and a plurality of fluid egress openings formed in the outer surface of the hollow tube that are in fluid communication with the elongated lumen of the hollow tube. In one embodiment, the fluid egress openings are evenly spaced from one another between the proximal and distal ends of the hollow tube.

In one embodiment, each of the fluid egress openings has the same size. In one embodiment, two or more of the fluid egress openings have different sizes. In one embodiment, the fluid egress openings have shapes selected from the group consisting of round holes and elongated slits.

In one embodiment, the elongated lumen of the hollow tube defines a cross-sectional diameter of about 0.25 mm, and the outer surface of the hollow tube defines a cross-sectional diameter of about 0.50 mm.

In one embodiment, an anchor is secured to the proximal end of the hollow tube.

In one embodiment, a surgical needle, such as a curved needle, is secured to the distal end of the hollow tube.

In one embodiment, a barbed microcatheter for delivering therapeutic fluids to tissue preferably includes a hollow tube having a proximal end, a distal end, and an elongated lumen disposed inside the hollow tube that extends between the proximal and distal ends of the hollow tube, a plurality of barbs projecting outwardly from an outer surface the hollow tube, and a plurality of fluid egress openings formed in the outer surface of the hollow tube that are in fluid communication with the elongated lumen of the hollow tube, whereby the fluid egress openings are evenly spaced from one another between the proximal and distal ends of the hollow tube.

In one embodiment, the barbed microcatheter preferably includes an anchor secured to the proximal end of the hollow tube, and a surgical needle secured to the distal end of the hollow tube.

In one embodiment, the barbed microcatheter preferably includes two or more fluid egress openings having different sizes including a first fluid egress opening located adjacent the anchor having a first size and a second fluid egress opening located adjacent the surgical needle having a second size that is smaller than the first size of the first fluid egress opening.

Infections associated with orthopedic implants can be disastrous for a patient, often resulting in severe consequences including reoperation, amputation, or death. Delivery of local antibiotics directly to the infected site at elevated doses, which would be hazardous if delivered systemically, but safe when delivered locally, can be accomplished using the microcatheters disclosed herein.

Inoperable tumors often leave patients with limited choices. Delivery of high dose chemotherapeutic agents or immune therapies (i.e. modified T-cells) directly to the tumor may provide a benefit not available before. The bioabsorbable microcatheters disclosed herein may be used to provide this type of local delivery of therapeutic fluids.

Post-op pain management with opioids is often not ideal for several reasons including risk of addiction, severe constipation, and cognitive impairment. Delivery of local anesthetics directly to the wound site with the microcatheters disclosed herein preferably provides a mechanism for reducing opioid use while minimizing patient pain and suffering.

In one embodiment, a barbed microcatheter may be coated and/or impregnated with an antimicrobial agent for preventing bacterial colonization. In one embodiment, a preferred antimicrobial agent is triclosan. In one embodiment, a vapor process may be used for applying a triclosan antimicrobial agent to a barbed microcatheter, such as a polymer barbed micocatheter made of polydioxanone or polycaprolactone. In one embodiment, antimicrobial agents used for barbed microcatheters may include, but are not limited to, triclosan, chlorohexadiene, povidone iodine, and/or silver compounds.

In one embodiment, a method of making a barbed microcatheter preferably includes forming a microcatheter blank (e.g., a polymer tube) concurrently with forming fluid egress openings (e.g., fluid emitting passages), or alternatively as a first prerequisite step to forming the fluid egress openings. In one embodiment, the microcatheter blank may be formed and strengthened with methods well-known in the art of polymer extrusion and polymer fiber drawing. In one embodiment, the microcatheter blank may be flattened to varying degrees to produce lateral, flattened regions that may be used to form barbs that project from a hollow tube.

In one embodiment, the sides of a microcatheter blank may be flattened, and the flattened sides sealed using thermal or ultrasonic energy. The cross-sectional shape of the microcatheter blank having the flattened sides may be heat set before or during a barb forming step to produce a microcatheter having an oval cross-section. In one embodiment, the microcatheter blank may be shielded from heat and allowed to spring back to a predominantly circular cross-section after barb formation.

In one embodiment, the fluid egress openings may be formed at the same time as any of the manufacturing steps disclosed herein, or may be accomplished in one or more separate steps as described herein.

In one embodiment, the barbed microcatheter disclosed herein preferably enables controlled and equal distribution of therapeutic fluids from fluid egress openings (e.g., holes, slits) that are located along the length of a hollow tube of the barbed microcatheter. In one embodiment, the fluid egress openings/slits are formed in a top side of a hollow tube of the barbed microcatheter. In one embodiment, the underside of the hollow tube has no fluid egress openings/slits.

In one embodiment, the cross-sectional area of the fluid egress openings may increase in size in relation to an increase in distance from a fluid source. In one embodiment, fluid egress openings that are closer to a fluid source may be smaller, and fluid egress openings that are further away from the fluid source may be larger. The sizes of the fluid egress openings may progressively increase along the length of the barbed microcatheter.

In one embodiment, the fluid egress openings formed in the hollow tube of the barbed microcatheter may include elongated slits. In one embodiment, the elongated slits may be substantially closed at lower fluid pressure levels (e.g., zero fluid pressure), however, the elongated slits preferably open when exposed to higher fluid pressure levels, which may be generated by a syringe or a fluid pump. Using elongated slits that open when exposed to higher pressure levels preferably enables an entire length of a microcatheter to first load up with therapeutic fluid at lower fluid pressure levels. Later, when higher fluid pressure levels have been attained, the elongated fluid egress slits will open for releasing the therapeutic fluid from the elongated fluid egress slits.

In one embodiment, a barbed microcatheter may have an anchor secured to one end and a needle (e.g., a curved needle) secured to the opposite end. In one embodiment, the anchor is secured to the proximal or trailing end of the barbed microcatheter and the needle is secured to the distal or leading end of the barbed microcatheter. In one embodiment, anchoring devices such as loops or reverse oriented barbs may be used. In one embodiment, double-armed and loop barbed symmetric catheters may also be manufactured.

In one embodiment, a barbed microcatheter may have fluid egress openings/holes having the same size. In one embodiment, a barbed microcatheter may have fluid egress openings/holes having various sizes.

In one embodiment, a barbed microcatheter may have fluid egress slits having the same length. In one embodiment, a barbed microcatheter may have fluid egress slits having various lengths.

In one embodiment, needles are used to form fluid egress openings in the hollow tube of a barbed microcatheter. In one embodiment, the diameters of the respective needles may vary along the length of the microcatheter to change the diameters of the respective fluid egress openings.

In one embodiment, forming dies may be configured to contain a barbed microcatheter after an initial forming step and hold the barbed microcatheter in a set position during a punching operation to form one or more fluid egress openings. In one embodiment, a fluid egress opening die may be used to simultaneously form a barbed microcatheter while punching the fluid egress openings.

In one embodiment, a forming die preferably has embedded hole punch needles that are located along the length of the barbed microcatheter that is contained within the forming die. The depth of insertion of the respective hole punch needles may vary along the length of the forming die to control the sizes (i.e., diameters) of the fluid egress openings. In one embodiment, the further a tapered point of a needle is inserted into the die, the larger the size of the fluid egress opening that is formed in the hollow tube of the barbed microcatheter.

In one embodiment, the hole punch needles are not be permanently affixed to the die, but rather may be made to move into a die cavity after the microcatheter (or microcatheter blank) has been inserted into the die. In one embodiment, the needles used to form the fluid egress openings may all articulate together, moving into and out of the die cavity together, or may be made to move in and out of the die individually.

In one embodiment, systems, devices and methods of making barbed microcatheters may include using one or more cutting blades for cutting slits into hollow tubes to form fluid egress slits. In one embodiment, the cutting blades may be affixed to at least one half of a die, or may be made to slide in and out of a die cavity, either simultaneously or individually. In one embodiment, the depth that the cutting blades are inserted into a die may be controlled to produce elongated slits of varying lengths. Forming elongated slits in hollow tubes of microcatheters will have minimal impact on the tensile strength of the microcatheters. In one embodiment, the elongated slits preferably provide a mechanism for controlling fluid flow rate, whereby the slits remain closed at low fluid pressure levels and open at incrementally higher fluid pressure levels for releasing the fluid.

In one embodiment, systems, devices and methods of forming elongated slits in the hollow tubes of microcatheters may involve inserting a cutting edge of a cutting blade into the outer wall of a hollow tube of a microcatheter and moving the cutting edge relative to the hollow tube for forming the elongated slit in the hollow tube. The cutting blade may articulate in two axes, or the cutting blade may be configured to move up and down while the die holding the microcatheter translates horizontally relative to the cutting blade.

In one embodiment, one or more cutting blades may be used to form barbs on the sides of a microcatheter. In one embodiment, the cutting blades may be used to form barbs that extend longitudinally, orthogonally, or at any angle in between the longitudinal and orthogonal orientations. A cross or "x-pattern" may also be produced with multiple passes of a cutting blade or via use of a specially shaped cutting blade.

In other embodiments, lasers and/or electron beams may be used for forming the barbs of a barbed microcatheter.

In one embodiment, a method of making a barbed microcatheter having fluid egress openings preferably includes compressing first and second lateral sides of a polymer blank to form a barbed microcatheter blank including a first flattened region extending along a first lateral side of the barbed microcatheter blank, a second flattened region extending along a second lateral side of the barbed microcatheter blank, and a hollow tube with an elongated lumen located between the first and second flattened regions.

In one embodiment, the method of making a barbed microcatheter having fluid egress openings may include removing material from the first and second flattened regions of the barbed microcatheter blank to form barbs that project outwardly from opposite sides of the hollow tube.

In one embodiment, the method of making a barbed microcatheter having fluid egress openings may include forming fluid egress openings in a wall of the hollow tube that are in fluid communication with the elongated lumen of the hollow tube.

In one embodiment, the method of making a barbed microcatheter having fluid egress openings may include compressing a proximal end of the polymer blank to form a tissue anchor connected with a proximal end of the hollow tube, and securing a needle to a distal end of the hollow tube.

In one embodiment, at least one cutting element is used for forming the fluid egress openings in the wall of the hollow tube.

In one embodiment, the step of forming fluid egress openings may include forming a first fluid egress opening in the wall of the hollow tube having a first size, and forming a second fluid egress opening is the wall of the hollow tube having a second size that is larger than the first size of the first fluid egress opening.

In one embodiment, the step of forming fluid egress openings may include forming a series of progressively larger fluid egress openings in the wall of the hollow tube.

In one embodiment, the fluid egress openings may be formed simultaneously during the forming fluid egress openings step.

In one embodiment, the fluid egress openings are formed independently of one another and at different times during the forming fluid egress openings step.

In one embodiment, the tissue anchor connected with the proximal end of the hollow tube preferably includes a flattened tab having a length and a width.

In one embodiment, the step of compressing the first and second lateral sides of the polymer blank may include placing the polymer blank into a pressing die having an upper pressing die part overlying the polymer blank and a lower pressing die part that opposes the upper pressing die part and that is located under the polymer blank. In one embodiment, the pressing die is preferably moved into a closed position for compressing upper and lower surfaces of the first and second lateral sides of the polymer blank for forming the first and second flattened regions and the hollow tube.

In one embodiment, the upper pressing die part preferably includes a plurality of cutting elements projecting from an underside of the upper pressing die part. In one embodiment, when the pressing die is in the closed position, the cutting elements engage the hollow tube for forming the fluid egress openings in the hollow tube.

In one embodiment, the removing material step preferably includes cutting the first and second flattened regions of the barbed microcatheter blank to form the barbs that project outwardly from the opposite sides of the hollow tube.

In one embodiment, the cutting step may include placing the barbed microcatheter blank including the first and second flattened regions and the hollow tube into a cutting die having an upper cutting die part and a lower cutting die part that opposes the upper cutting die part, and moving the cutting die into a closed position for cutting the first and second flattened regions of the barbed microcatheter blank for forming the barbs that project outwardly from the opposite sides of hollow tube.

In one embodiment, the upper cutting die part preferably includes a plurality of cutting elements projecting from an underside of the upper cutting die part. In one embodiment, when the cutting die is in the closed position the cutting elements engage the hollow tube for forming the fluid egress openings in the hollow tube.

In one embodiment, pressing rollers may be used on the polymer blank for compressing upper and lower surfaces of the first and second lateral sides of the polymer blank for forming the first and second flattened regions and the hollow tube of the barbed microcatheter blank.

In one embodiment, a method of making a barbed microcatheter having fluid egress openings desirably includes obtaining a barbed microcatheter blank including a hollow tube having a proximal end, a distal end, and an elongated lumen that extends between the proximal and distal ends of the hollow tube, and first and second flattened regions that extend along opposite sides of the hollow tube.

In one embodiment, the method of making a barbed microcatheter may include removing material from the first and second flattened regions of the barbed microcatheter blank to form barbs projecting outwardly from the opposite sides of the hollow tube, using one or more cutting elements for forming fluid egress openings in a wall of the hollow tube that are in fluid communication with the elongated lumen of the hollow tube, forming a tissue anchor that is connected with the proximal end of the hollow tube, and securing a surgical needle with the distal end of the hollow tube.

In one embodiment, a method of delivering a therapeutic fluid to tissue preferably includes positioning a barbed microcatheter adjacent a wound having a first wound end and a second wound end, whereby the barbed microcatheter may include a hollow tube having an elongated lumen extending between first and second ends of the hollow tube, barbs projecting outwardly from opposite sides of the hollow tube, fluid egress openings formed in the hollow tube that are in fluid communication with the elongated lumen, a tissue anchor secured to the first end of the hollow tube, and a needle secured to the second end of the hollow tube.

In one embodiment, a method of delivering a therapeutic fluid to tissue may include using the needle to form a first tissue opening at the first end of the wound and pulling the hollow tube completely through the first tissue opening until the tissue anchor abuts against tissue at the first end of the wound.

In one embodiment, a method of delivering a therapeutic fluid to tissue may include using the needle to form a second tissue opening at the second end of the wound and pulling the hollow tube completely through the second tissue opening so that the barbs projecting outwardly from opposite sides of the hollow tube engage tissue within the wound that is located between the first and second ends of the wound.

In one embodiment, a method of delivering a therapeutic fluid to tissue desirably includes passing the needle through a skin layer of a patient so that the needle and the second end of the hollow tube are located outside the patient.

In one embodiment, a method of delivering a therapeutic fluid to tissue may include cutting the second end of the hollow tube for detaching the needle from the hollow tube, and introducing a therapeutic fluid into the cut second end of the hollow tube so that the therapeutic fluid flows into the elongated lumen and passes through the fluid egress openings for infusing the wound with the therapeutic fluid.

In one embodiment, after the needle has passed through the skin layer for being located outside the patient, an intermediate section of the hollow tube containing the barbs and the fluid egress openings is preferably located between the first and second ends of the wound.

In one embodiment, after the barbed microcatheter has been positioned within the wound, the intermediate section of the hollow tube is disposed within the closed wound.

In one embodiment, after the barbed microcatheter has been positioned within the wound, the intermediate section of the hollow tube extends along a linear path between the first and second ends of the wound.

In one embodiment, after the barbed microcatheter has been positioned within the wound, the intermediate section of the hollow tube extends along a non-linear path between the first and second ends of the wound.

These and other preferred embodiments of the present patent application will be described in more detail herein.

BRIEF DESCRIPTION OF THE DRAWINGS

FIG. 16 is a top plan view of a barbed microcatheter having spaced fluid egress openings, in accordance with one embodiment of the present patent application.

DETAILED DESCRIPTION OF PREFERRED EMBODIMENTS

Figure 1:
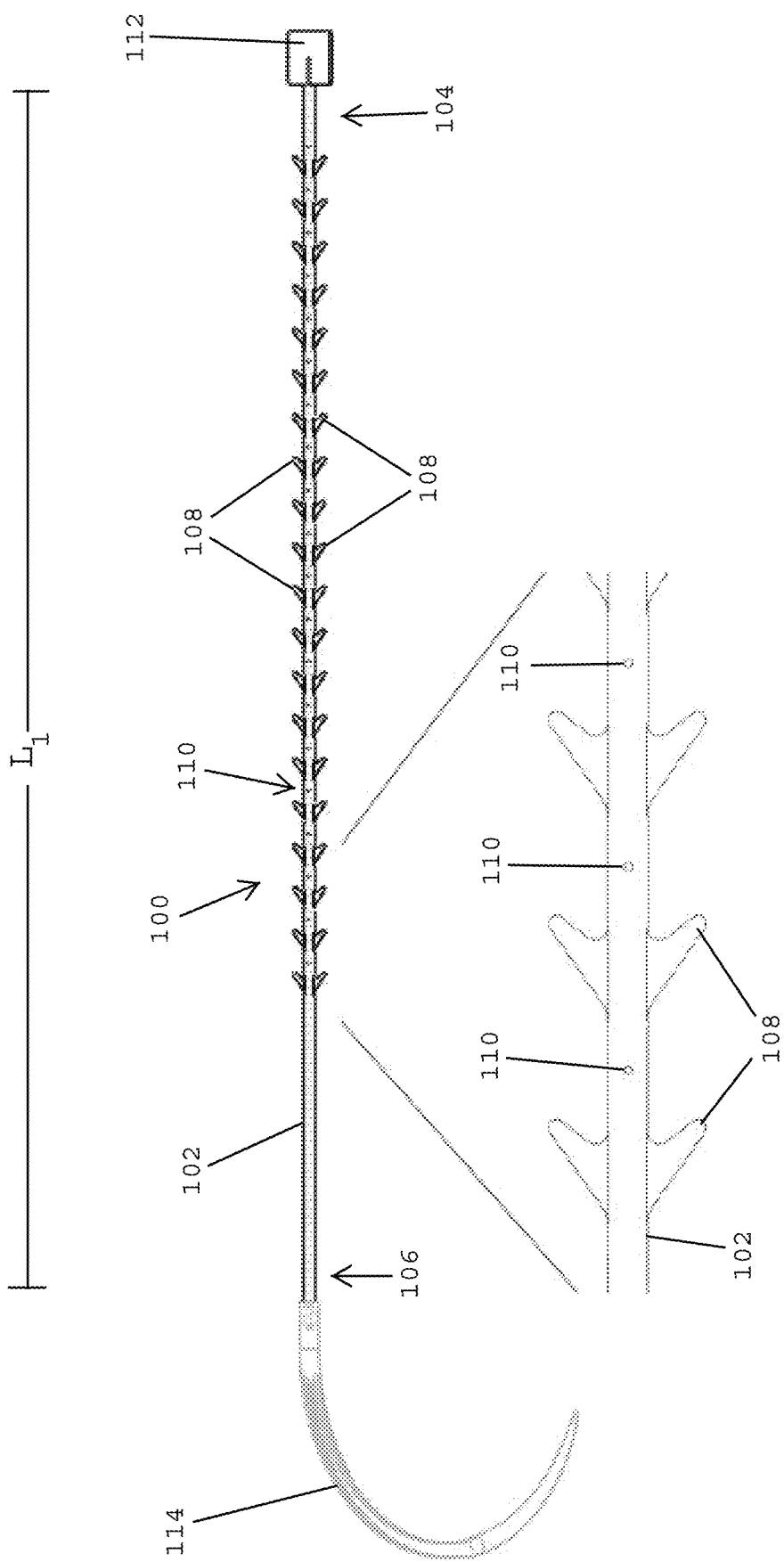
FIG. 1 is a top view of a barbed microcatheter having fluid egress openings, in accordance with one embodiment of the present patent application.

Referring to FIG. 1, in one embodiment, a barbed microcatheter 100 preferably includes a hollow tube 102 having a proximal end 104 and a distal end 106. In one embodiment, the barbed microcatheter 100 preferably has a length $L_1$ of about 2-12 inches, and more preferably about 7-8 inches. The barbed microcatheter 100 desirably includes barbs 108 that are spaced from one another along the length of the hollow tube 102 and that project from opposite sides of the hollow tube. In one embodiment, the barbed microcatheter includes a plurality of fluid egress openings 110 that are formed in the outer wall of the hollow tube 102, and that are spaced from one another along the length of the hollow tube.

In one embodiment, the hollow tube 102 has an elongated lumen extending along the length of the hollow tube. The fluid egress openings 110 are preferably in fluid communication with the elongated lumen so that fluid flowing through the elongated lumen of the hollow tube may pass out of the hollow tube via the fluid egress openings. In one embodiment, the barbed microcatheter 100 may included a tissue anchor 112 that is secured to the proximal end 104 of the hollow tube 102, and a surgical needle 114 that is secured to the distal end 106 of the hollow tube 102.

Referring to FIGS. 2A-2E, in one embodiment, the barbed microcatheter 100 preferably includes the hollow tube 102 with the fluid egress openings 110 formed in the outer wall 116 of the hollow tube 102. In one embodiment, the fluid egress openings 110 are preferably spaced from one another along the length of the hollow tube 102. In one embodiment, the fluid egress openings 110 are round holes. In one embodiment, the outer wall 116 of the hollow tube 102 has an outer surface 118 and an inner surface 120 that surrounds the elongated lumen 122 of the hollow tube 102. The elongated lumen preferably extends along the length of the hollow tube and is in fluid communication with the spaced fluid egress openings so that fluid (e.g., a therapeutic fluid) may be dispensed from the barbed microcatheter.

In one embodiment, the barbed microcatheter 100 preferably includes a plurality of barbs 108 that extend from the sides of the hollow tube 102. The plurality of barbs 108 are preferably spaced from one another along the length of the hollow tube 102. In one embodiment, the barbs 108 may be symmetrically arranged in pairs of barbs that are spaced from one another along the length of the hollow tube, whereby the barbs of each pair extend away from one another on opposite sides of the hollow tube 102.

Figure 2A:
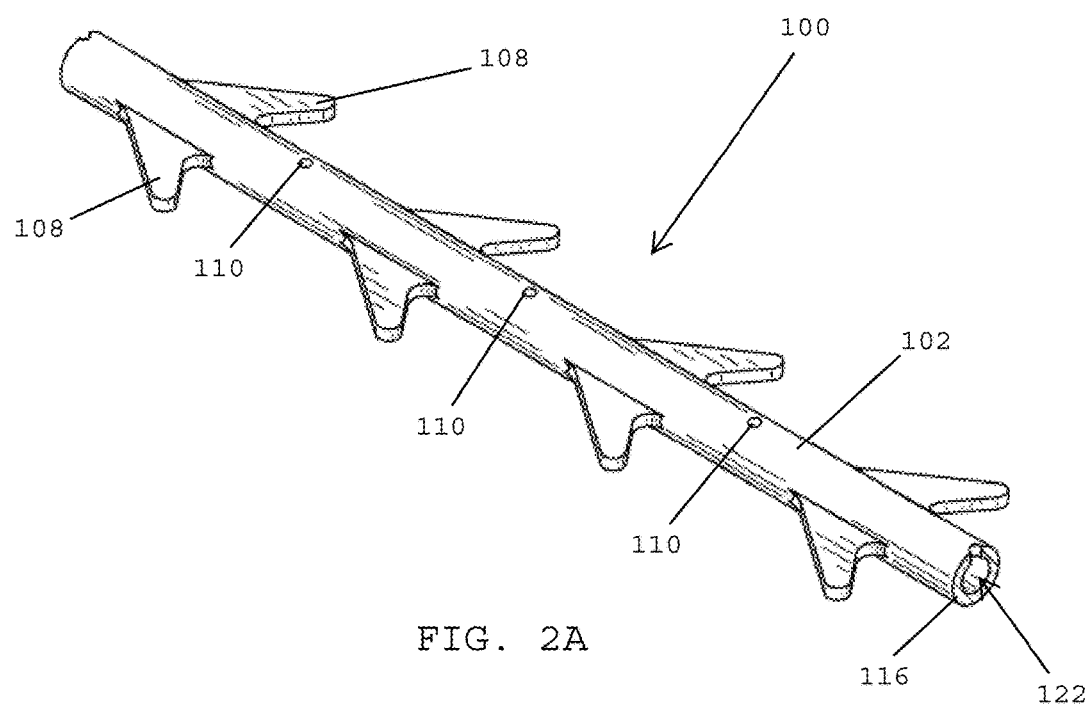
FIG. 2A is a perspective view of a barbed microcatheter having fluid egress openings, in accordance with one embodiment of the present patent application.
Figure 2B:
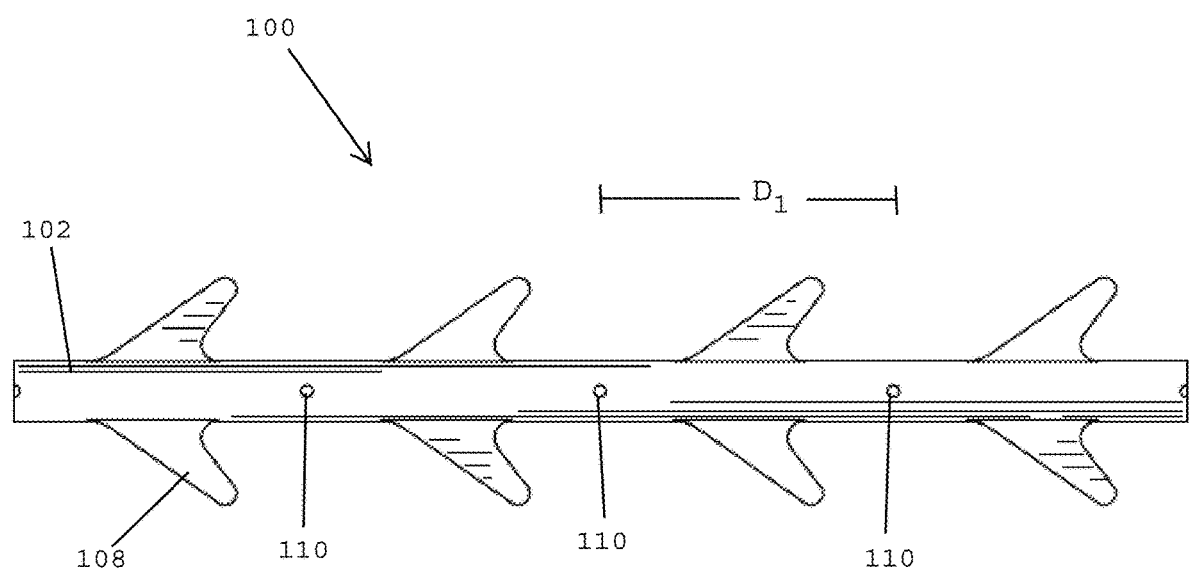
FIG. 2B is a top plan view of the barbed microcatheter shown in FIG. 2A.

Referring to FIG. 2B, in one embodiment, the fluid egress openings 110 (e.g., round holes having diameters) are spaced from one another along the length of the hollow tube 102 of the barbed microcatheter 100. In one embodiment, the distance $D_1$ between adjacent, spaced fluid egress openings 110 may be about 4-25 millimeters, and more preferably about 4-12 millimeters. In one embodiment, the spaced fluid egress openings 110 may be the same size (i.e., same diameter). In one embodiment, the spaced fluid egress openings 110 may have different sizes (i.e., different diameters).

Figure 2C:
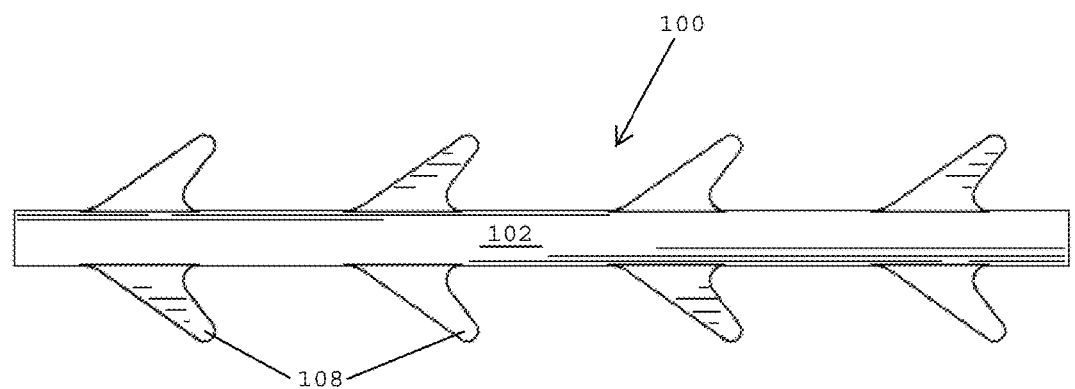
FIG. 2C is a bottom view of the barbed microcatheter shown in FIGS. 2A-2B.

Referring to FIGS. 2B and 2C, in one embodiment, the fluid egress openings 110 are desirably formed in a topside of the hollow tube 102 of the barbed microcatheter 100. In one embodiment, the fluid egress openings are formed in a top side of a hollow tube with no openings being formed on the underside of the hollow tube. FIG. 2C shows an underside of the hollow tube 102 of the barbed microcatheter having no fluid egress openings formed therein.

Figure 2D:
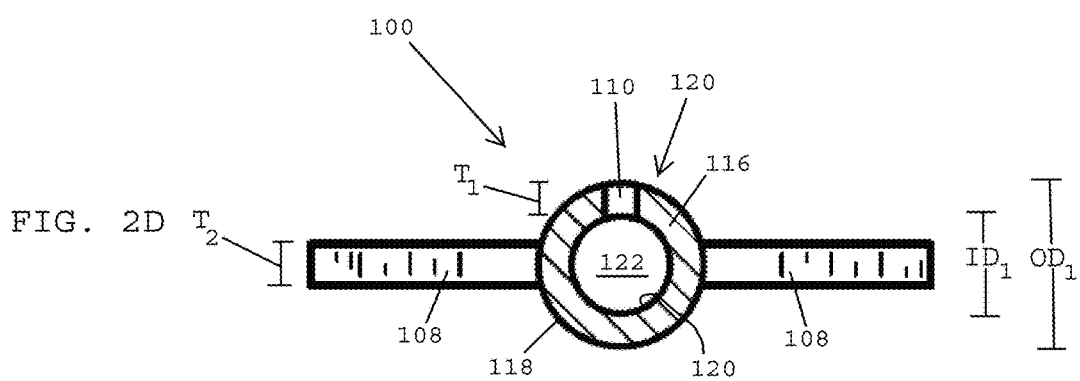
FIG. 2D is a proximal end view of the barbed microcatheter shown in FIG. 2A-2C.
Figure 2E:
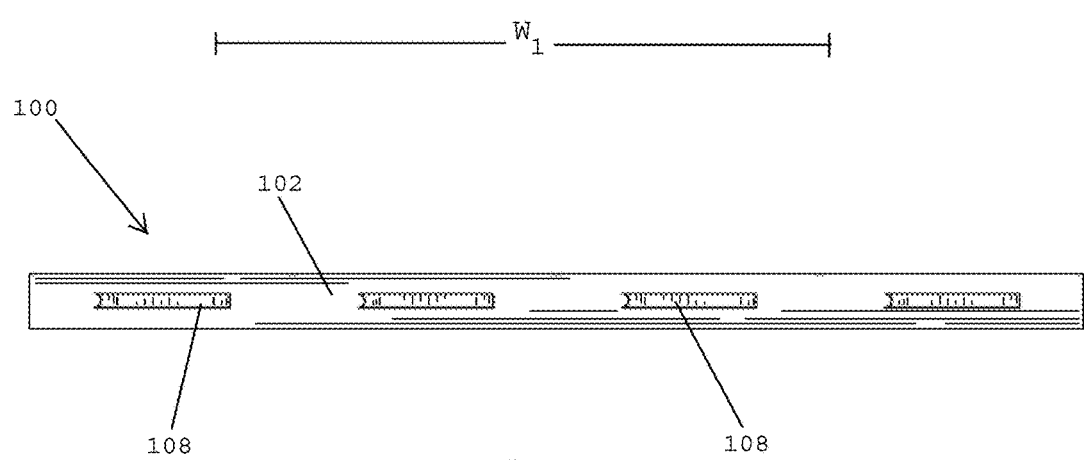
FIG. 2E is a left side view of the barbed microcatheter shown in FIGS. 2A-2D.

Referring to FIG. 2D, in one embodiment, the hollow tube 102 of the barbed microcatheter 100 preferably includes the outer wall 116 having an outer surface 118 and an inner surface 120 that surrounds the elongated lumen 122. In one embodiment, the fluid egress opening 110 that is formed in the topside of the outer wall 116 of the hollow tube 102. In one embodiment, the fluid egress opening 110 is desirably in fluid communication with the elongated lumen 122 extending along the length of the hollow tube so that fluid within the elongated lumen may be dispensed via the fluid egress opening 110.

In one embodiment, the outer surface 118 of the outer wall 116 of the hollow tube 102 defines an outer diameter $OD_1$ of about 0.5 millimeters. In one embodiment, the inner surface 120 of the outer wall 116 of the hollow tube 102 defines an inner diameter $ID_1$ of about 0.25 millimeters. In one embodiment, the outer diameter $OD_1$ defined by the outer wall of the hollow tube is about 2× greater than the inner diameter $ID_1$ defined by the inner surface of the outer wall of the hollow tube. In one embodiment, the outer wall 116 of the hollow tube preferably has a thickness $T_1$ of about 0.125 millimeters.

Referring to FIGS. 2A-2E, in one embodiment, the barbed microcatheter 100 preferably includes the barbs 108 that project from opposite sides of the hollow tube 102. The barbs are preferably spaced from another on each side of the hollow tube. In one embodiment, the barbs have a thickness $T_2$ that is at least 10% of the size of the outer diameter $OD_1$ of the hollow tube 102. In one embodiment, the thickness $T_2$ of the barbs 108 may be about 0.05-0.20 millimeters. In one embodiment, a pair of barbs 108 may define a tip-to-tip width $W_1$ of about 1-3 mm.

Figure 3:
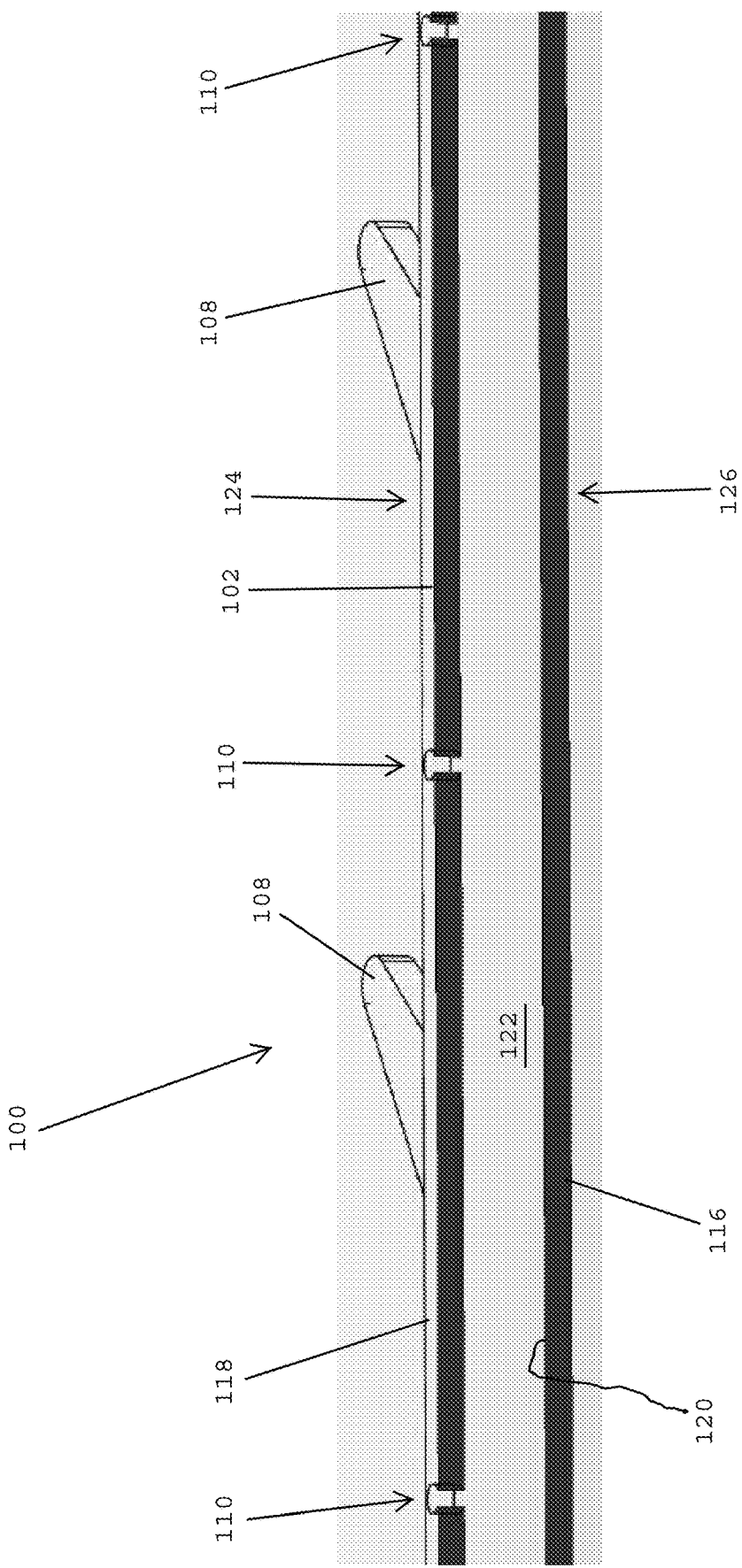
FIG. 3 is a cross-sectional view of the barbed microcatheter shown in FIGS. 2A-2E.

Referring to FIG. 3, in one embodiment, the barbed microcatheter 100 (FIGS. 2A-2E) preferably includes the hollow tube 102 having an outer wall 116 with an outer surface 118 and an inner surface 120 that surrounds the elongated lumen 122 that extends along the length of the hollow tube 102. The barbed microcatheter 100 preferably includes the fluid egress openings 110 that are spaced from one another along the length of the hollow tube 102. In one embodiment, the fluid egress openings 110 are formed in a topside 124 of the hollow tube 102. In one embodiment, the hollow tube 102 has an underside 126 that is devoid of the fluid egress openings provided at the topside 124.

In one embodiment, the fluid egress openings 110 pass completely through the thickness $T_1$ of the outer wall 116 of the hollow tube 102 so that the fluid egress openings 110 are in fluid communication with the elongated lumen 122 that extends along the length of the hollow tube. In one embodiment, the barbed microcatheter 100 may be implanted into tissue, and a fluid, such as a therapeutic fluid, may be introduced into the elongated lumen 122 of the hollow tube 102, whereupon the fluid passes through the fluid egress openings 110 for bathing bath tissue that surrounds the hollow tube. In one embodiment, the barbed microcatheter 100 preferably includes the barbs 108 that are spaced from one another along the length of the hollow tube 102. In one embodiment, after the barbed microcatheter 100 has been implanted into tissue, the barbs 108 projecting from the sides of the hollow tube 102 preferably engage the surrounding tissue for holding the hollow tube in place within the tissue.

In one embodiment, a barbed microcatheter having fluid egress openings is preferably made of an absorbable, biocompatible polymer material. The absorbable polymers may include conventional biocompatible, polymers such as lactide, polylactic acid, polyglycolic acid, glycolide, polydioxanone, polycaproactone, copolymers and blends thereof and the like.

In one embodiment, a barbed microcatheter may be coated and/or impregnated with an antimicrobial agent for preventing bacterial colonization. In one embodiment, a preferred antimicrobial agent is triclosan. In one embodiment, a vapor process may be used for applying a triclosan antimicrobial agent to a barbed microcatheter, such as a polymer barbed micocatheter made of polydioxanone or polycaprolactone. In one embodiment, antimicrobial agents used for barbed microcatheters may include, but are not limited to, triclosan, chlorohexadiene, povidone iodine, and/or silver compounds.

Figure 4A:
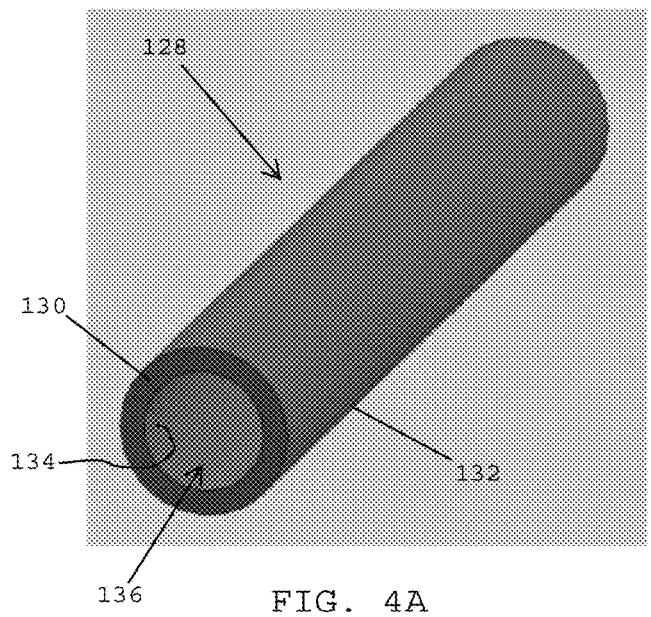
FIG. 4A is a perspective view of a microcatheter blank used to form a barbed microcatheter having fluid egress openings, in accordance with one embodiment of the present patent application.
Figure 4B:
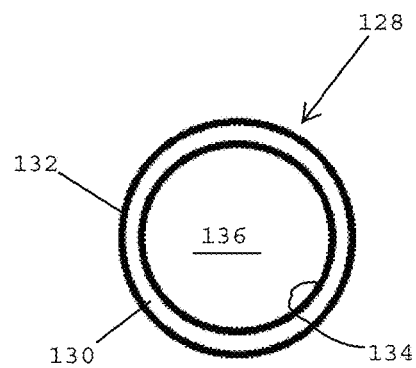
FIG. 4B is a cross-sectional view of the microcatheter blank shown in FIG. 4A.

Referring to FIGS. 4A and 4B, in one embodiment, the barbed microcatheter 100 shown and described above in FIGS. 1-3 may be made by first forming a microcatheter blank 128 having an outer wall 130 with an outer surface 132, an inner surface 134, and an elongated lumen 136 that extends along the length of the microcatheter blank 128. As used herein, the term blank means an object (e.g., a hollow tube precursor) intended for further shaping or finishing to make a final product (e.g., a barbed microcatheter having fluid egress openings). The microcatheter blank may be drawn for controlling the molecular orientation of the particles of the microcatheter blank, which preferably enhances the strength of the microcatheter blank. As will be described in more detail herein, the microcatheter blank 128 may be subjected to additional processing steps (e.g., shaping, cutting, puncturing) for making a final product or medical device, namely, a barbed microcatheter having barbs and egress openings.

Figure 5:
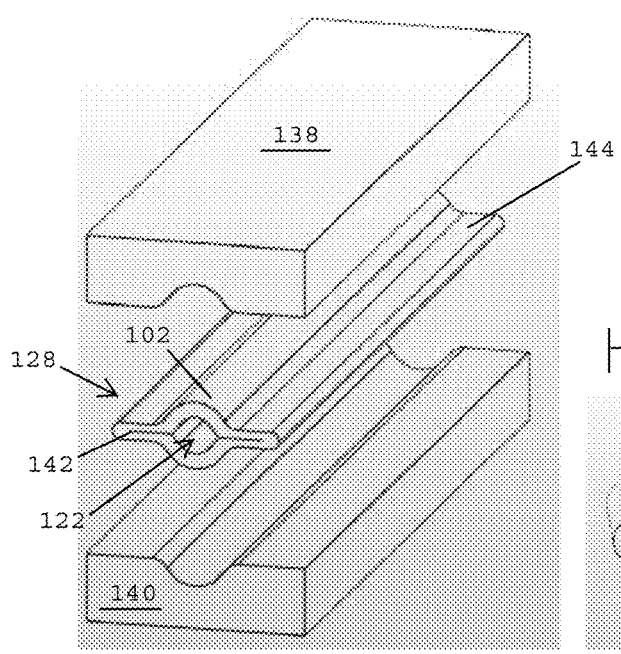
FIG. 5 is a perspective view of a pressing die used to form a microcatheter blank having flattened lateral regions that extend along the length of the microcatheter blank, in accordance with one embodiment of the present patent application.

Referring to FIG. 5, in one embodiment, the microcatheter blank 128 is preferably disposed between an upper die 138 and a lower die 140 of a press or pressing die. In one embodiment, the upper and lower die 138, 140 preferably move toward one another for compressing and/or shaping the microcatheter blank 128 therebetween. In one embodiment, when the upper and lower die 138, 140 are moved into a closed position, the die compress the microcatheter blank 128 to form a first flattened region 142 and a second flattened region 144 that extend along the sides of the microcatheter blank 128. In one embodiment, the first and second flattened regions 142, 144 preferably extend along the length of the microcatheter blank. In one embodiment, the upper and lower die 138, 140 preferably have opposing faces that shape a central portion of the microcatheter blank 128 into a hollow tube 102 of the barbed microcatheter shown and described above in FIGS. 2A-2E and 3. The hollow tube 102 preferably includes the elongated lumen 122 that extends along the length thereof.

Figure 6:
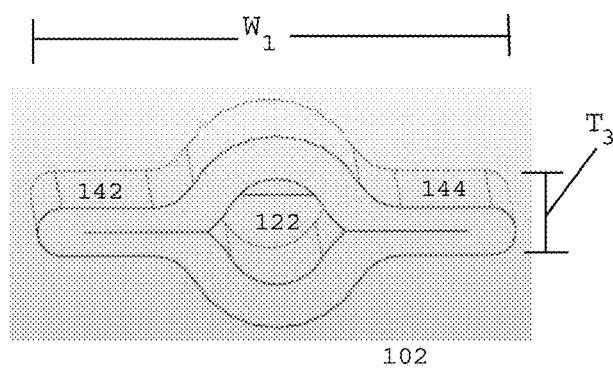
FIG. 6 is a perspective view of a microcatheter blank having flattened lateral regions that extend along the length of the microcatheter blank, in accordance with one embodiment of the present patent application.

FIG. 6 shows an end view of the microcatheter blank 128 after it has been shaped and/or formed by the upper and lower die 138, 140 shown in FIG. 5. The microcatheter blank 128 desirably includes the first flattened region 142 that extends along one side of the microcatheter blank 128 and a second flattened region 144 that extends along an opposite, second side of the microcatheter blank. The hollow tube 102 shown and described above in FIGS. 2A-2E and 3 preferably extends along the length of the microcatheter blank 128. The hollow tube 102 desirably has the elongated lumen 122 that extends along the length of the hollow tube 102. The pressed microcatheter blank 128 with the first and second flattened regions 142, 144 preferably has a width $W_2$ of about 0.75-3 mm. The first and second flattened regions 142, 144 preferably have a thickness $T_2$ that is about 10-30% of the outer diameter $OD_1$ of the hollow tube 102.

Figure 7:
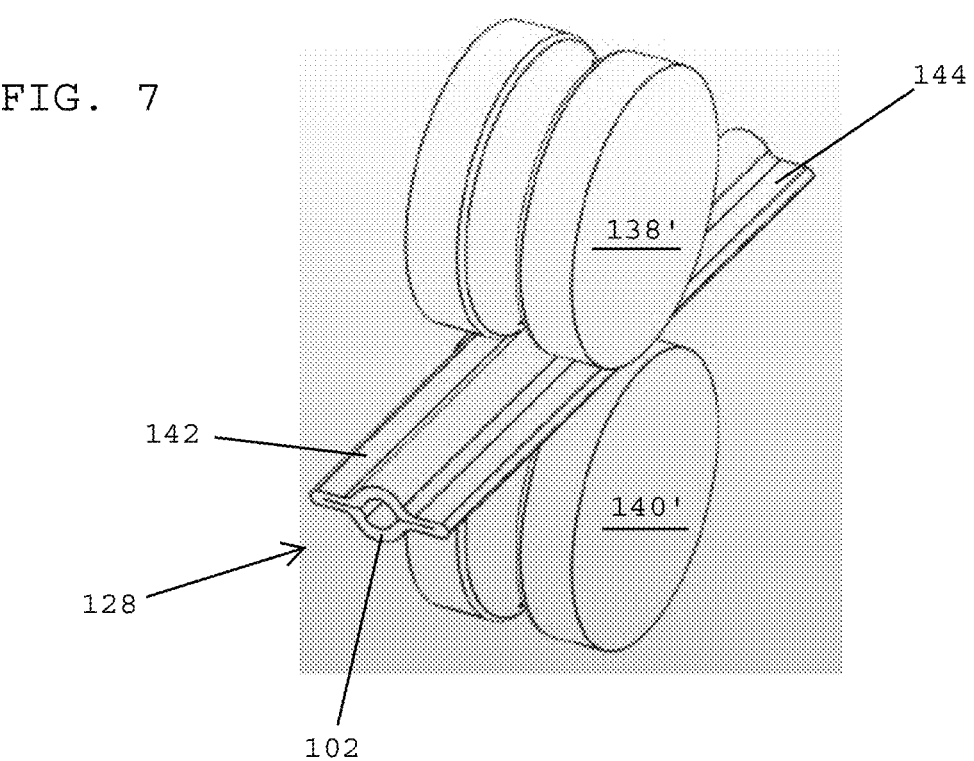
FIG. 7 is a perspective view of pressing rollers used to form a microcatheter blank having flattened lateral regions that extend along the length of the microcatheter blank, in accordance with one embodiment of the present patent application.

Referring to FIG. 7, in one embodiment, rather than using the upper and lower pressing die 148, 150 shown in FIG. 5, the microcatheter blank 128 shown and described above in FIG. 6 may be formed using opposing pressing rollers 138', 140' that engage the top and bottom sides of the microcatheter blank 128 for forming the first and second flattened regions 142, 144 (FIG. 6), as well as the hollow tube 102 shown and described above in FIGS. 2A-2E and 3.

Figure 8:
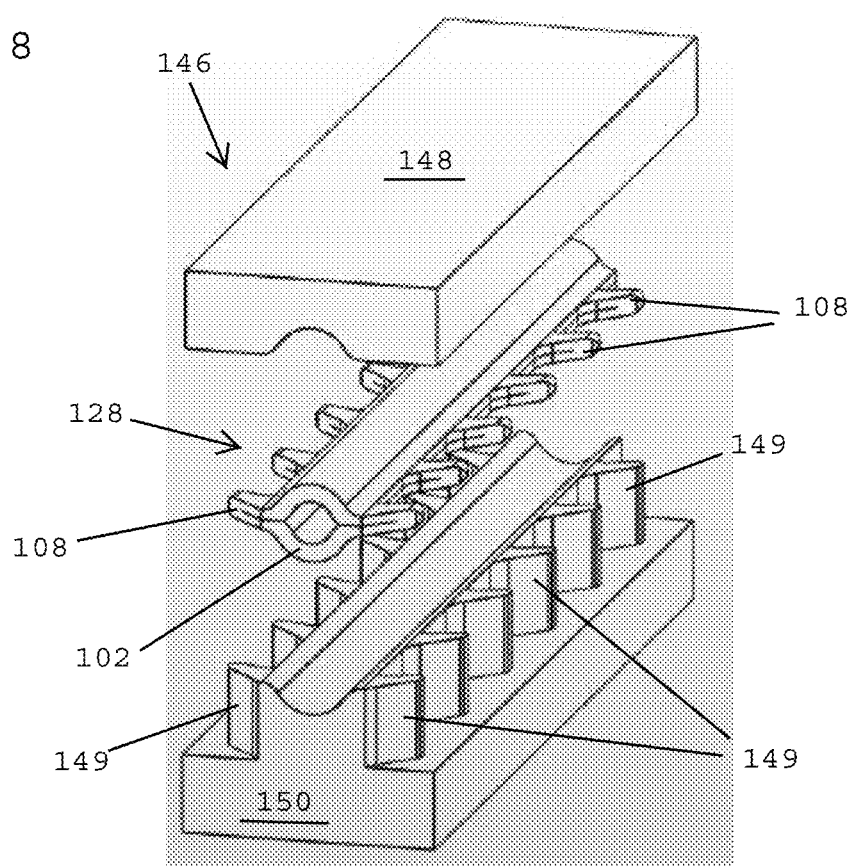
FIG. 8 is a perspective view of cutting die used to cut barbs in flattened lateral regions that extend along the length of a microcatheter blank, in accordance with one embodiment of the present patent application.

Referring to FIG. 8, in one embodiment, the microcatheter blank 128 with the flattened regions 142, 144 (FIG. 6) may be placed into a cutting die 146 having an upper cutting die 148 and a lower cutting die 150 having cutting teeth 149. In one embodiment, the upper and lower cutting die 148, 150 may be moved into a closed position, whereupon the cutting teeth 149 engage the first and second flattened regions 142, 144 (FIG. 7) of the microcatheter blank 128 (FIG. 6) for forming the barbs 108 (FIG. 2A) that extend along the length of the hollow tube 102. In one embodiment, rather than using a cutting die, the barbs 108 may be formed using a cutting instrument such as a razor blade that cuts the first and second flattened regions 142, 144 (FIG. 6) of the microcatheter blank 128 to form the barbs. In one embodiment, the barbs 108 may be formed using one or more lasers that cut the first and second flattened regions 142, 144 (FIG. 6) of the microcatheter blank 128.

Figure 9:
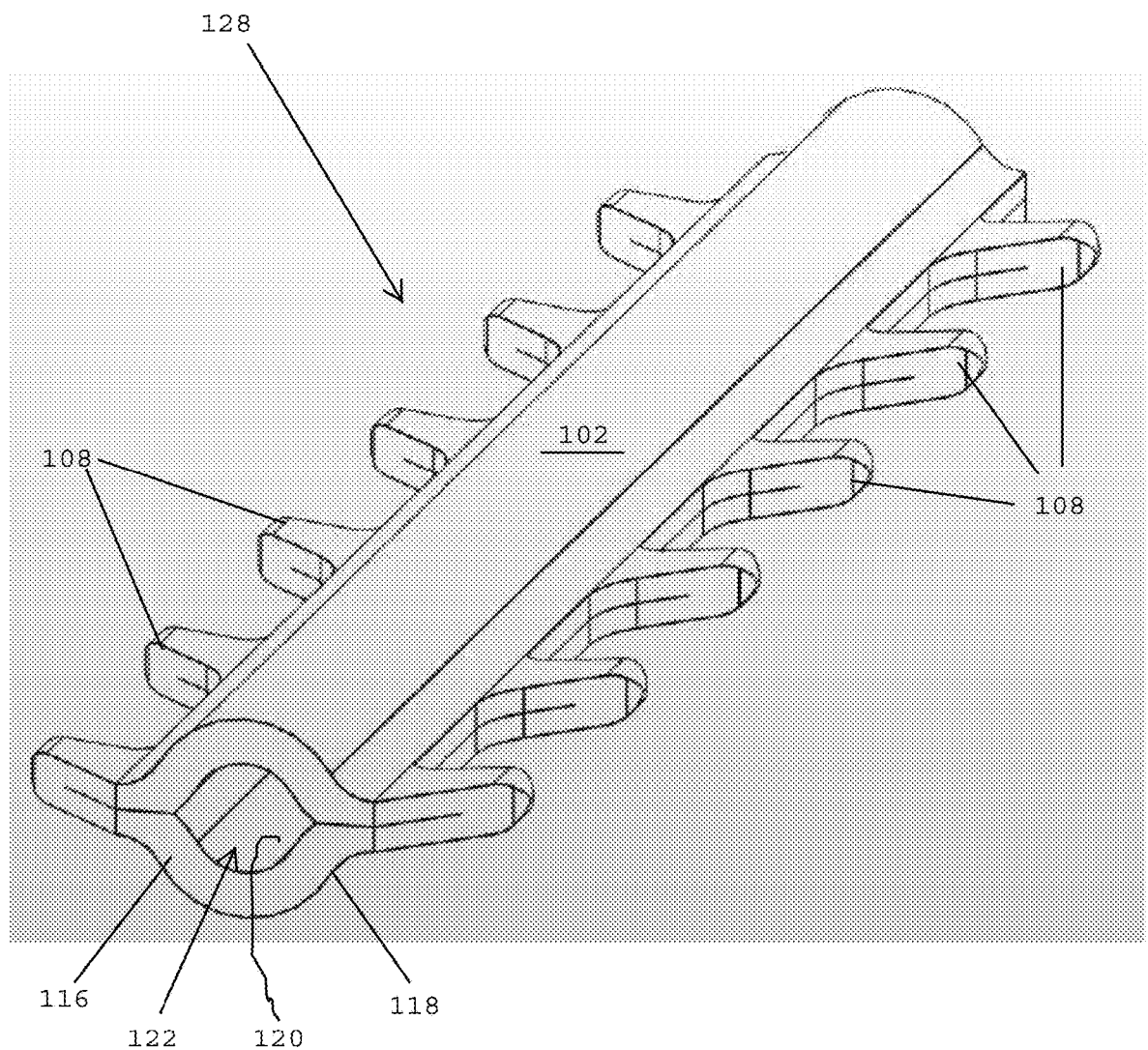
FIG. 9 is a perspective view of the microcatheter blank having barbs shown in FIG. 8.

Referring to FIG. 9, in one embodiment, after the barbs 108 are formed from the first and second flattened regions 142, 144 (FIG. 6), the microcatheter blank 128 preferably includes the hollow tube 102 having the spaced barbs 108 projecting from opposite sides of the hollow tube 102. The hollow tube 102 preferably includes an outer wall 116 having an outer surface 118 and an inner surface 120 that defines an elongated lumen 122 that extends along the length of the hollow tube 102.

Figure 10A:
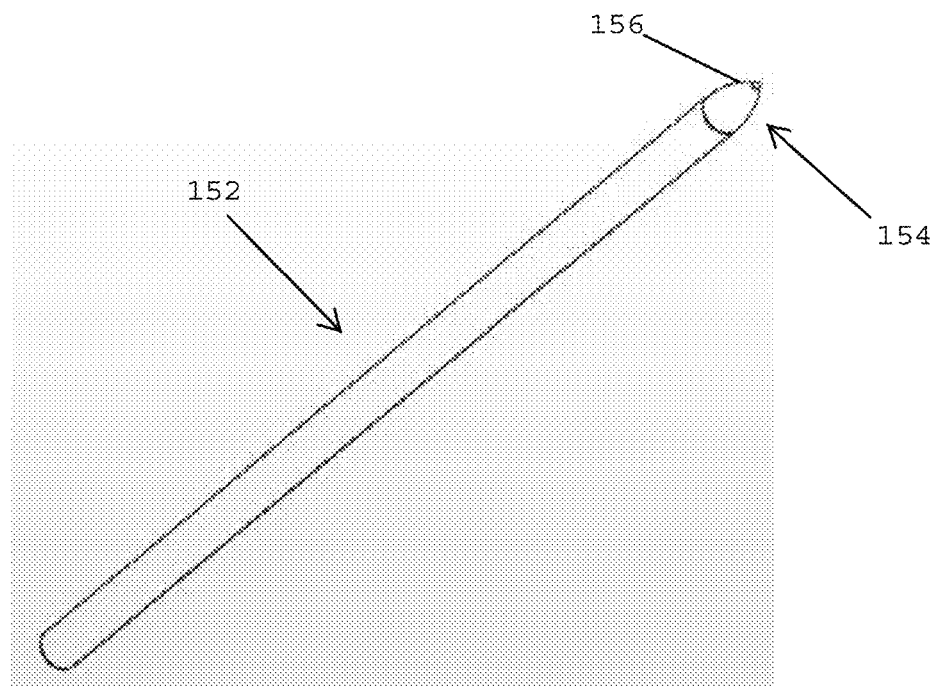
FIG. 10A is a perspective view of a needle used for forming fluid egress openings in the microcatheter blank of FIG. 9, in accordance with one embodiment of the present patent application.
Figure 10B:
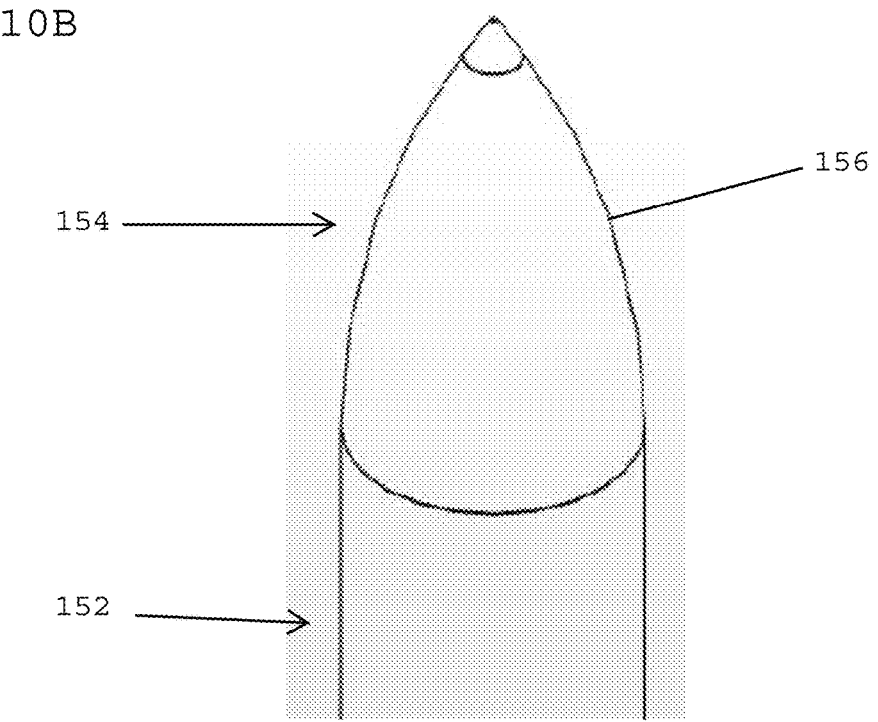
FIG. 10B is a magnified view of a distal end of the needle shown in FIG. 10A.

Referring to FIGS. 10A and 10B, in one embodiment, a needle 152 having a pointed tip 154 may be utilized for forming the fluid egress openings 110 (FIG. 2A) in the outer wall of the hollow tube 102 (FIG. 9). The pointed tip 154 of the needle 152 preferably has a tapered region 156 so that the cross-sectional diameter of the needle 152 increases in size between the distal-most end of the tapered region 156 and the proximal end of the tapered region 156. The tapered region 156 of the pointed tip 154 preferably enables fluid egress openings to be formed in the hollow tube of the barbed microcatheter, as will be described in more detail herein. Moreover, in one embodiment, the tapered region 156 of the pointed tip 154 preferably enables fluid egress openings of different sizes (e.g., different diameters) to be formed in the hollow tube of the barbed microcatheter. Thus, the needle 152 may be used to form fluid egress openings having the same size or fluid egress openings having different sizes.

Figure 11:
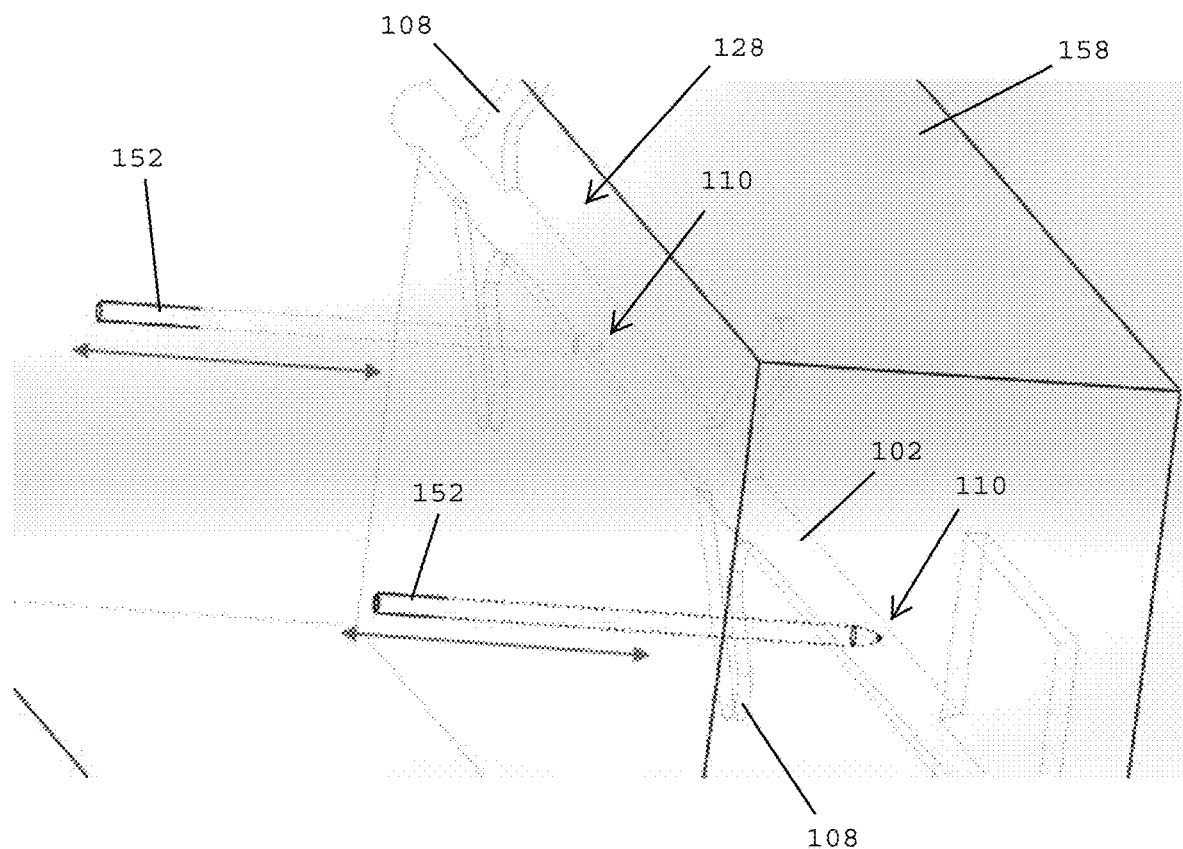
FIG. 11 is a perspective view of a die used for forming a barbed microcatheter having fluid egress openings, in accordance with one embodiment of the present patent application.

Referring to FIG. 11, in one embodiment, the microcatheter blank 128 (FIG. 9) having the hollow tube 102 and the barbs 108 extending from the sides thereof may be placed into a fluid egress opening die 158 that is used for forming the fluid egress openings 110 (FIG. 2A) in the hollow tube 102. In one embodiment, one or more of the needles 152 shown and described above in FIGS. 10A-10B may be introduced into the fluid egress opening die 158 to make the fluid egress openings 110 in the hollow tube 102 of the microcatheter blank 128. In one embodiment, the needles 152 may be slid into and out of the fluid egress opening die and/or rotated about their longitudinal axes for forming the fluid egress openings 110 in the hollow tube 102 of the microcatheter blank.

Figure 12:
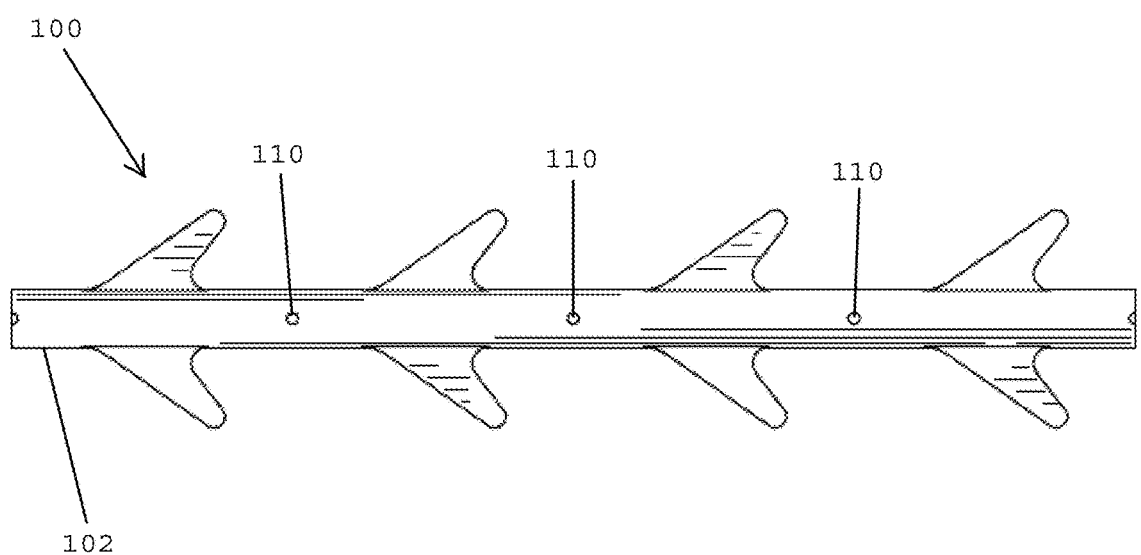
FIG. 12 is a top plan view of a barbed microcatheter having fluid egress openings formed in a top side of a hollow tube, in accordance with one embodiment of the present patent application.

Referring to FIG. 12, in one embodiment, after the needles 152 (FIG. 11) and the fluid egress opening die 158 of FIG. 11 have been utilized for forming the fluid egress openings 110 in the hollow tube 102, the microcatheter blank shown in FIG. 9 is preferably transformed into a barbed microcatheter 100 having spaced fluid egress openings 110. In one embodiment, the fluid egress openings 110 may be round holes or circular openings that are formed in the outer wall of the hollow tube 102. The fluid egress openings 110 may be evenly spaced from one another along the length of the hollow tube. The fluid egress openings 110 may have the same size, or may have different sizes. In one embodiment, the size of the fluid egress openings increases between the distal end and the proximal end of the hollow tube.

In one embodiment, the pressing die shown in FIG. 5, the pressing rollers shown in FIG. 7, and the cutting die shown in FIG. 8 may have needles incorporated therein, whereupon the fluid egress openings may be formed at the same time that the first and second flattened regions 142, 144 (FIGS. 5 and 7) are formed, or at the same time that the barbs 108 are cut (FIG. 8).

Figure 13:
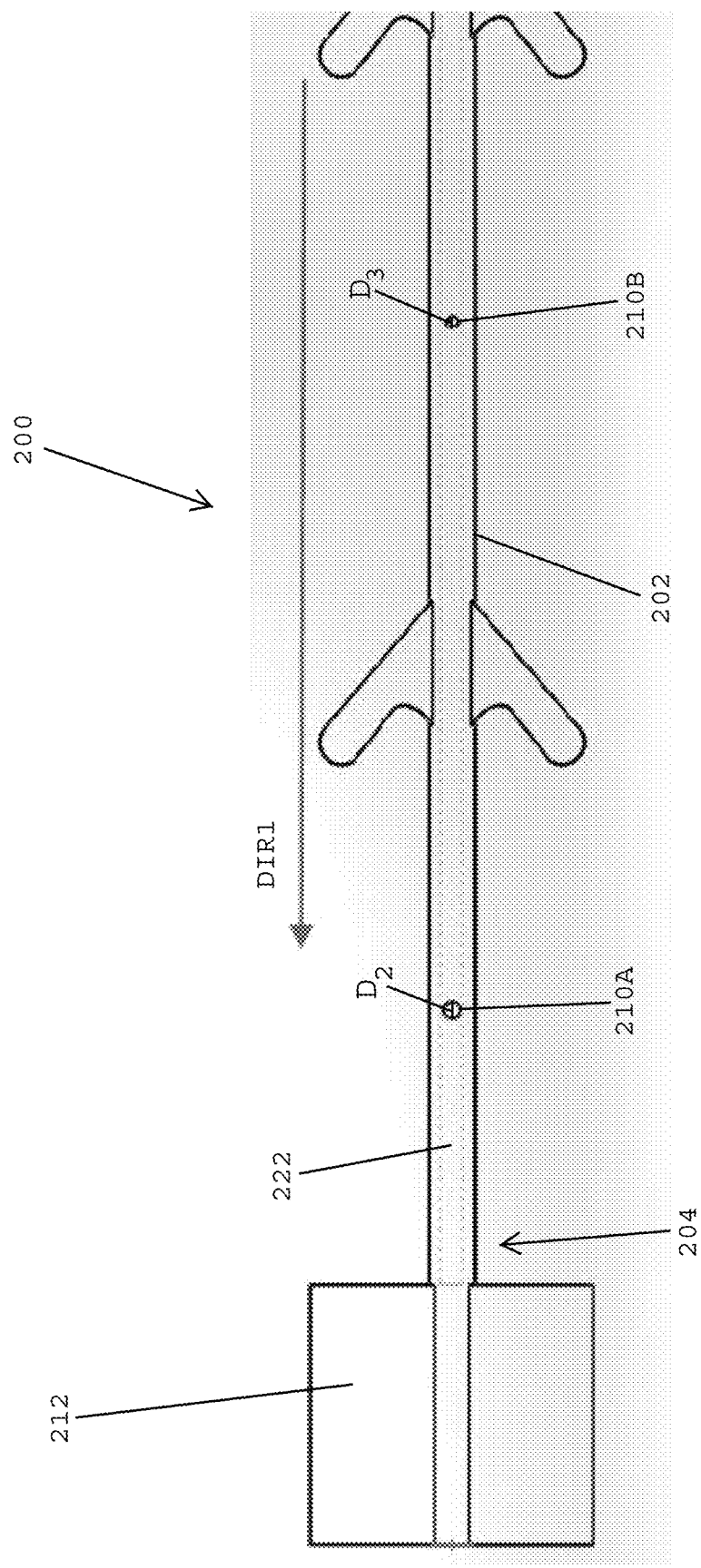
FIG. 13 is a top plan view of a barbed microcatheter having a hollow tube with spaced fluid egress openings having different sizes, in accordance with one embodiment of the present patent application.

Referring to FIG. 13, in one embodiment, a barbed microcatheter 200 preferably includes a hollow tube 202 having an elongated lumen 222 extending along the length thereof. In one embodiment, the barbed microcatheter 200 preferably includes fluid egress openings 210 that are spaced from one another along the length of the hollow tube 202. In one embodiment, the diameters of the respective fluid egress openings 210 may changes in size between a proximal end of the hollow tube 202 (e.g., the end adjacent a tissue anchor) and a distal end of the hollow tube 202 (e.g., the end adjacent a surgical needle). In one embodiment, a first fluid egress opening 210A that is closer to the proximal end 204 of the hollow tube 202 (e.g., the end closer to the tissue anchor) has a first diameter $D_2$ that is larger than a second fluid egress opening 210B having a second diameter $D_3$. The sizes of the fluid egress openings may become progressively smaller along the length of the hollow tube (e.g., progressively smaller between the proximal end the distal end of the hollow tube), with smaller openings near a fluid source and larger openings further away from the fluid source for maintaining a constant flow of fluid from the fluid egress openings.

Figure 14A:
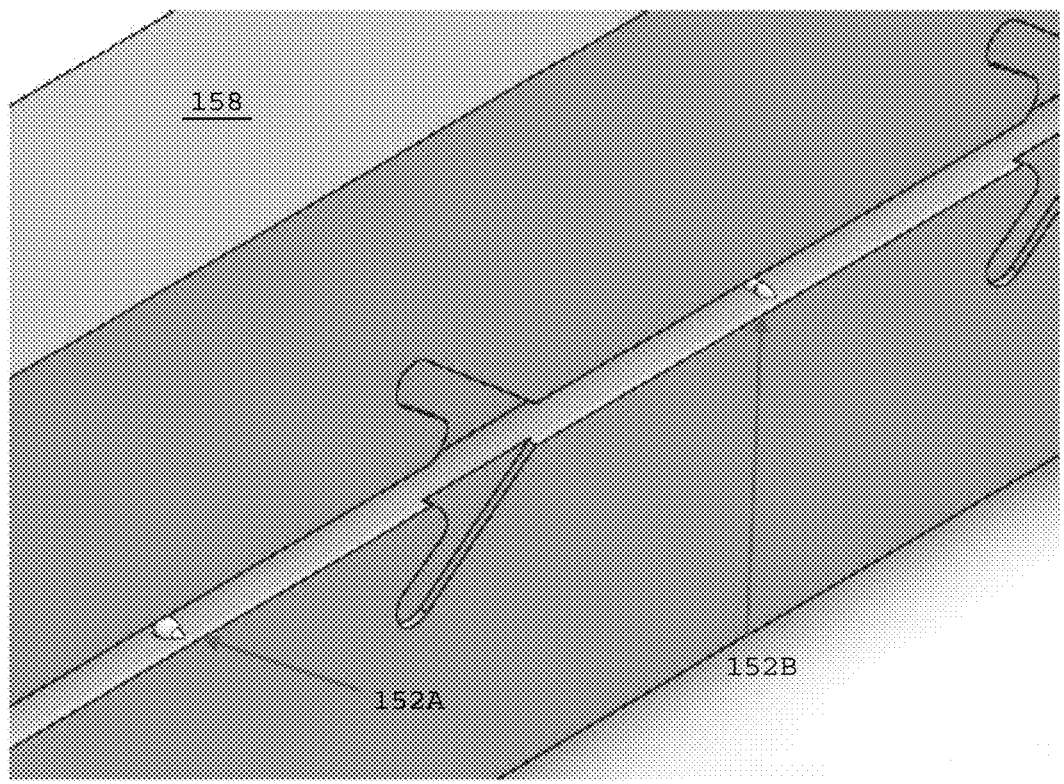
FIG. 14A is a perspective view of a die used for forming spaced fluid egress openings in a hollow tube of a barbed microcatheter, in accordance with one embodiment of the present patent application.
Figure 14B:
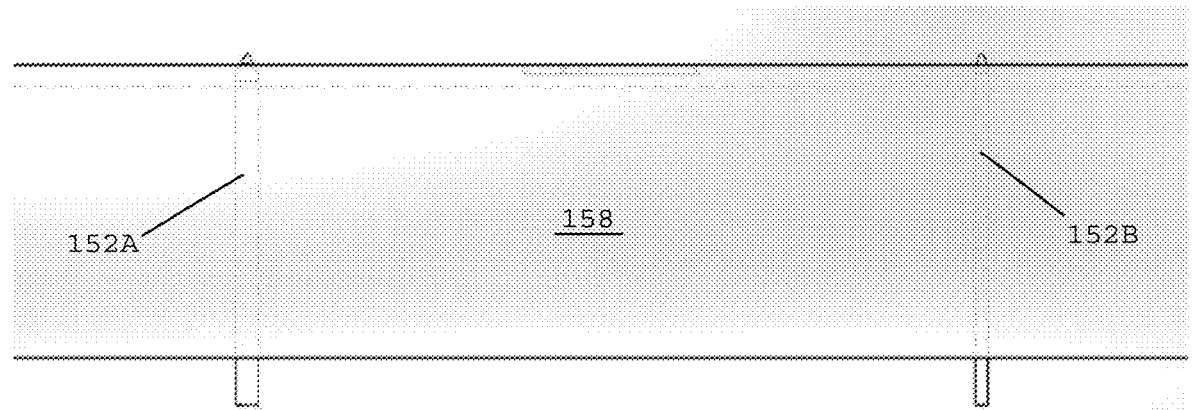
FIG. 14B is a side view of the die shown in FIG. 14A.

Referring to FIGS. 14A and 14B, in one embodiment, the fluid egress opening die 158 shown and described above in FIG. 11 may be utilized for forming the fluid egress openings in the hollow tube of the barbed microcatheter. In one embodiment, a pair of needles 152A, 152B having the same diameter may be utilized for puncturing the hollow tube for forming fluid egress openings having different sizes. In one embodiment, the first needle 152A is inserted to a greater depth than a second needle 152B. The size of the hole will depend on how far the needle is pushed into the hollow tube. As a result, the first fluid egress opening 210A (FIG. 13) formed by the first needle 152A will have a greater diameter and/or size than the second fluid egress opening 210B (FIG. 13) formed by the second needle 152B. In one embodiment, a plurality of needles (e.g., 10-50) may be used for forming a plurality of spaced fluid egress openings that extend along the length of the barbed microcatheter. The needles may operate together or independently of one another for forming the spaced fluid egress openings.

Figure 15A:
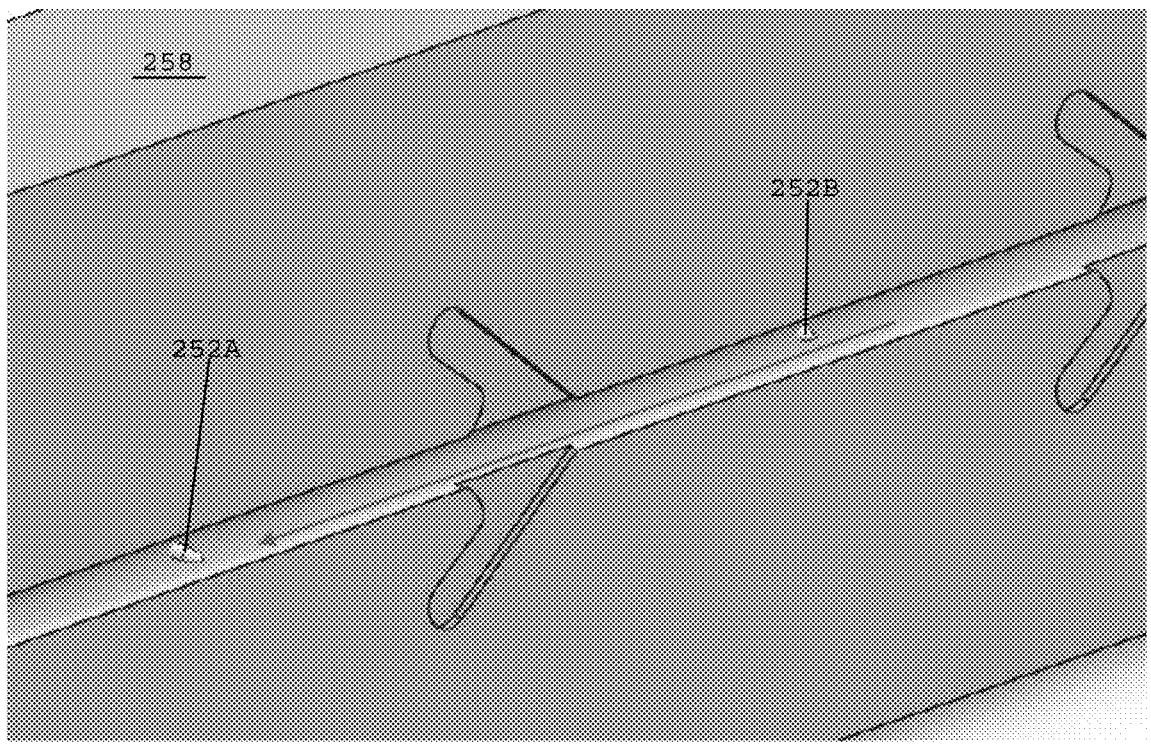
FIG. 15A is a perspective view of a die used for forming spaced fluid egress openings in a hollow tube a barbed microcatheter, in accordance with one embodiment of the present patent application.
Figure 15B:
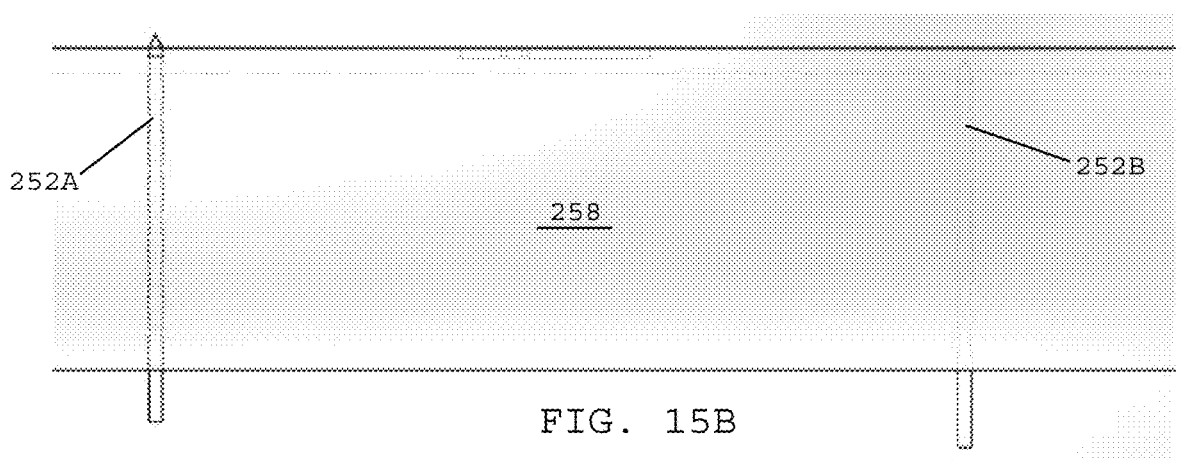
FIG. 15B is a side view of the die shown in FIG. 15A.
Figure 17A:
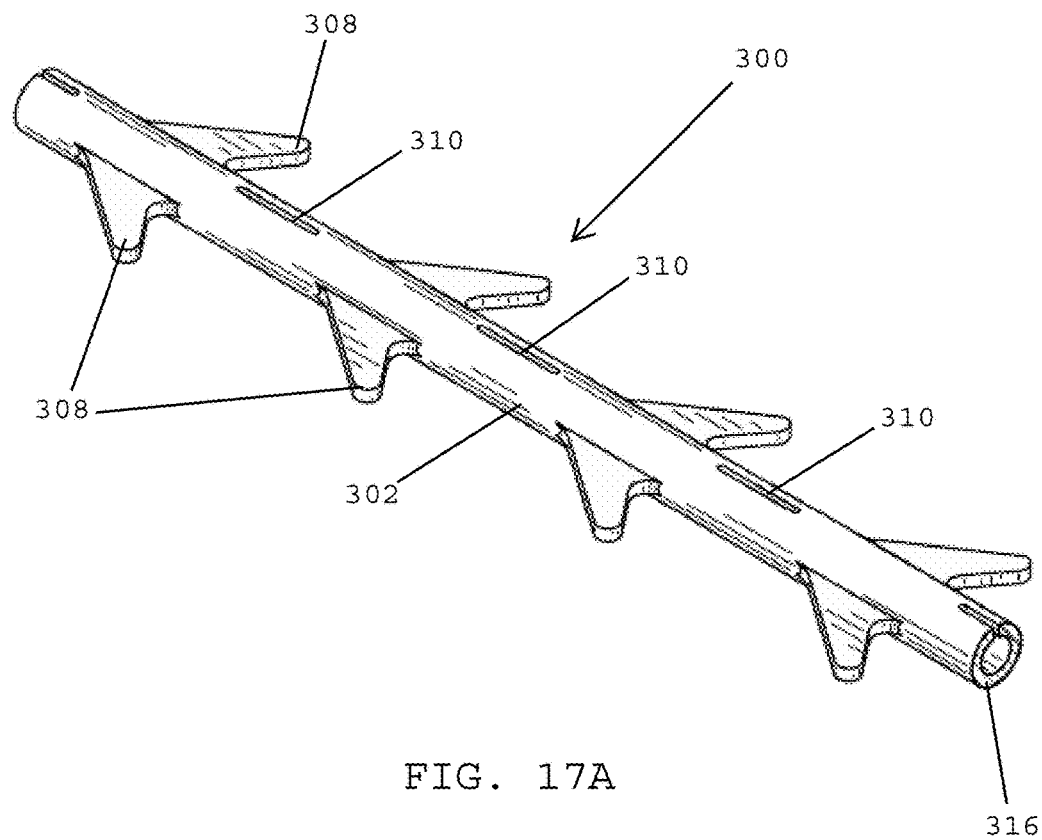
FIG. 17A is a perspective view of a barbed microcatheter having spaced egress slits, in accordance with one embodiment of the present patent application.
Figure 17B:
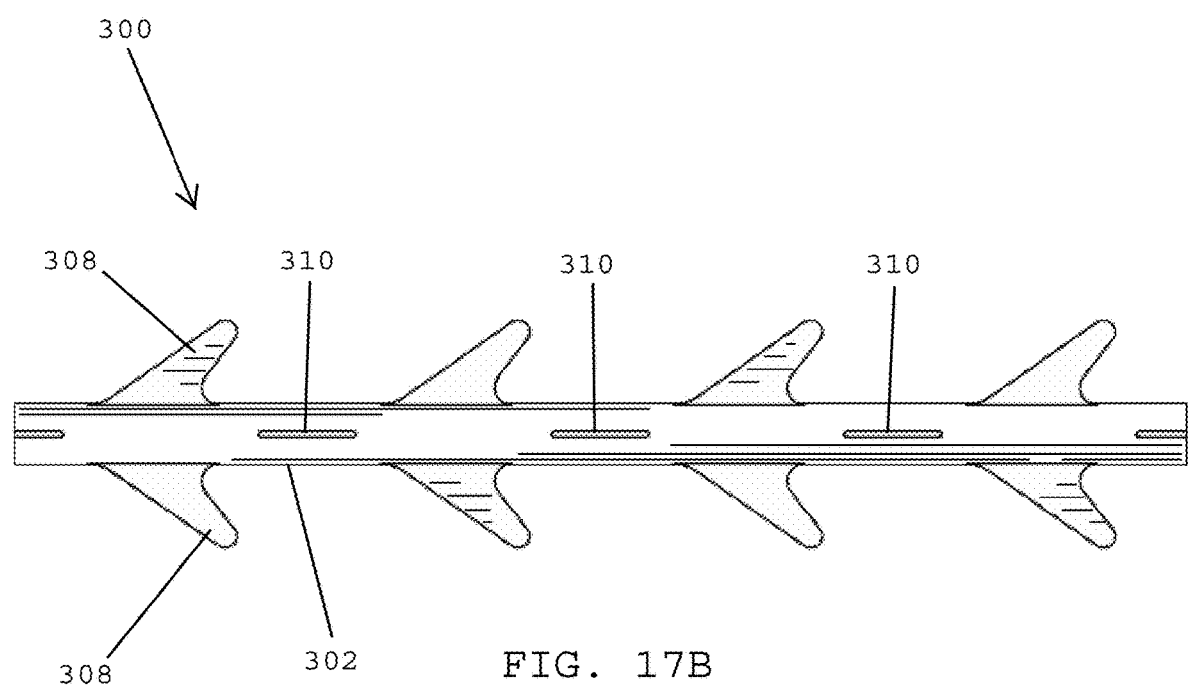
FIG. 17B is a top plan view of the barbed microcatheter shown in FIG. 17A.
Figure 17C:
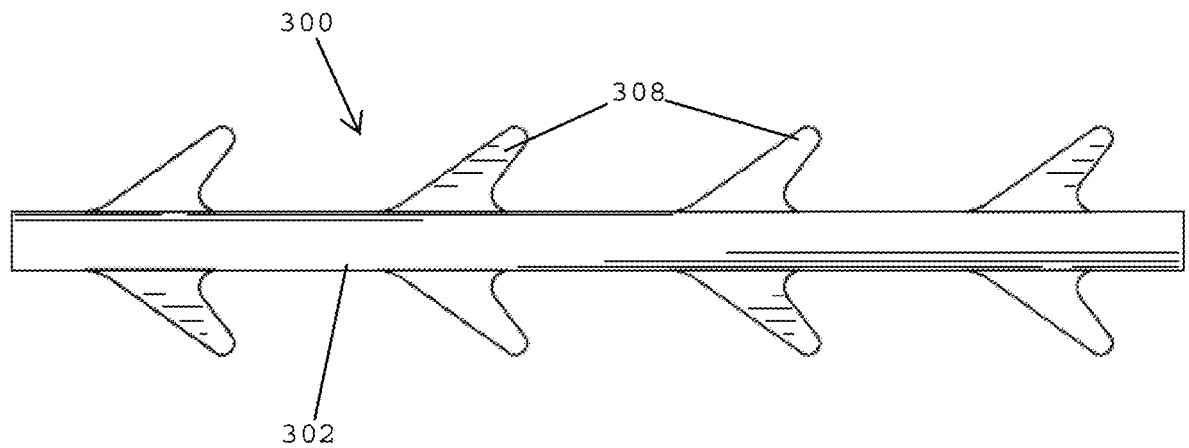
FIG. 17C is a bottom view of the barbed microcatheter shown in FIGS. 17A-17B.
Figure 17D:
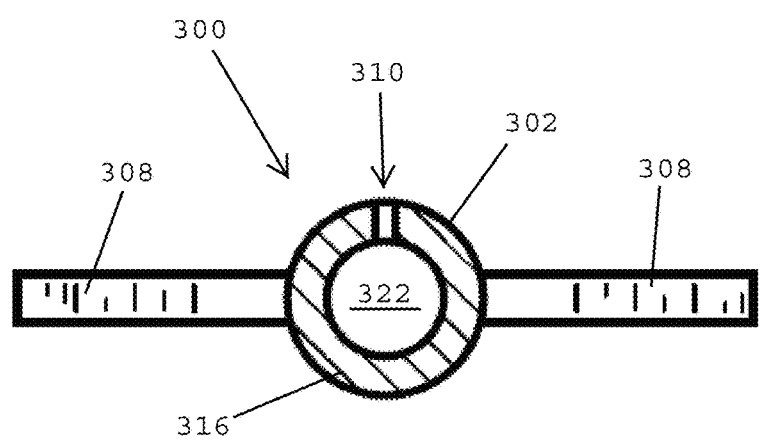
FIG. 17D is a proximal end view of the barbed microcatheter shown in FIGS. 17A-17C.
Figure 17E:
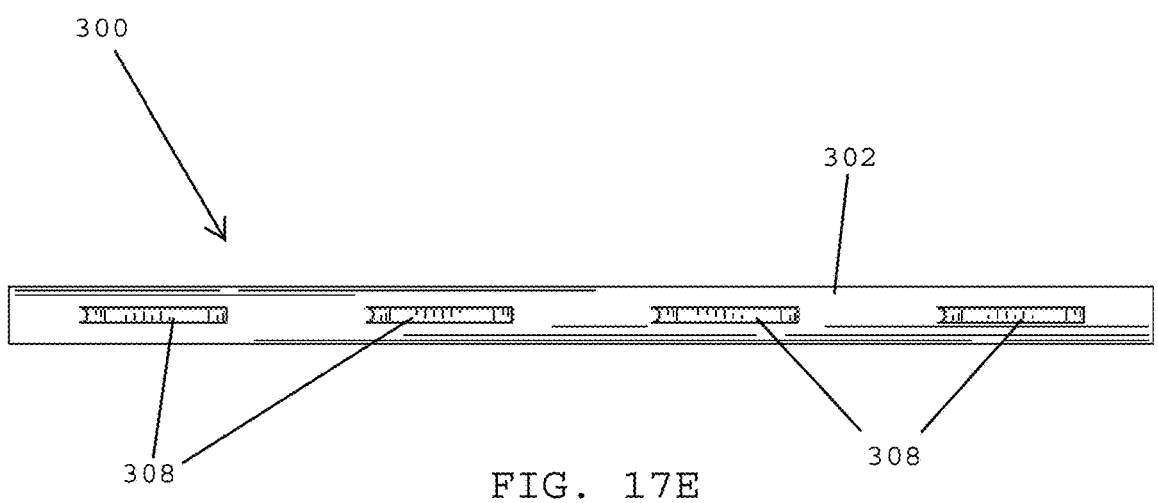
FIG. 17E is a left side view of the barbed microcatheter shown in FIGS. 17A-17D.

Referring to FIGS. 15A and 15B, in one embodiment, a fluid egress opening die 258 may be used for forming barbed microcatheters having fluid egress openings having different sizes. In one embodiment, the fluid egress opening die 258 may include a larger diameter needle 252A and a smaller diameter needle 252B. In one embodiment, the larger diameter needle 252A is advanced into the fluid egress opening die 258 to puncture the hollow tube to form a larger, first fluid egress opening 210A (FIG. 13) in the barbed microcatheter, while the smaller diameter needle 252B may be utilized for puncturing the hollow tube for forming a smaller, second fluid egress opening 210B in the barbed microcatheter. In one embodiment, a fluid egress opening die may include a plurality of needles (e.g., 10-50 needles) having progressively larger diameters for forming fluid egress openings having progressively larger sizes and/or diameters.

In one embodiment, the fluid egress openings of a barbed microcatheter may include one or more elongated slits. Referring to FIG. 16, in one embodiment, a barbed microcatheter 300 preferably includes a hollow tube 302 having a proximal end 304 and a distal end 306. The barbed microcatheter 300 desirably has a plurality of barbs 308 projecting from opposite sides of the hollow tube 302. The barbs 308 are spaced from one another along the length of the hollow tube 302. In one embodiment, the barbed microcatheter 300 desirably includes fluid egress slits 310 that are formed in the hollow tube 302 and that are spaced from one another along the length of the hollow tube 302. In one embodiment, the spaced fluid egress slits 310 are desirably elongated slits that are formed (e.g., cut, punctured) in the outer wall of the hollow tube 302, whereby the slits are desirably in fluid communication with an elongated lumen that extends along the length of the hollow tube 302. The longitudinal axes of the respective fluid egress slits 310 may extend along and/or be parallel with a longitudinal axis of the hollow tube 302.

In one embodiment, the barbed microcatheter desirably includes a tissue anchor 312 that is secured to the proximal end 304 of the hollow tube 302 and a surgical needle 314 that is secured to the distal end 306 of the hollow tube 302. The surgical needle 314 may be utilized for positioning the barbed microcatheter 300 in tissue. After being implanted in tissue, the barbs 308 preferably hold the barbed microcatheter in place in the tissue.

Referring to FIGS. 17A-17E, in one embodiment, the barbed microcatheter 300 preferably includes the hollow tube 102 having the fluid egress slits 310 extending through the outer wall 316 of the hollow tube 302. The barbed microcatheter 300 desirably includes pairs of barbs 308 that extend from opposite sides of the hollow tube 302. The pairs of barbs are preferably spaced from one another along the length of the hollow tube. With the exception of the fluid egress slits 310 formed on the topside of the hollow tube 302, the barbed microcatheter 300 shown and described in FIGS. 17A-17E may have similar dimensions and/or features as the barbed microcatheters shown and described above in FIGS. 1-3.

Referring to 17D, in one embodiment, the fluid egress slits 310 preferably pass completely through the outer wall 316 of the hollow tube 302 for providing fluid communication between the elongated lumen 322 of the hollow tube 302 and the fluid egress slits 310. As a result, fluid passing through the elongated lumen 322 of the hollow tube 302 may flow through the fluid egress slits 310 for bathing tissue that surrounds the outside of the hollow tube 302 with the fluid disposed within the elongated lumen.

Figure 18:
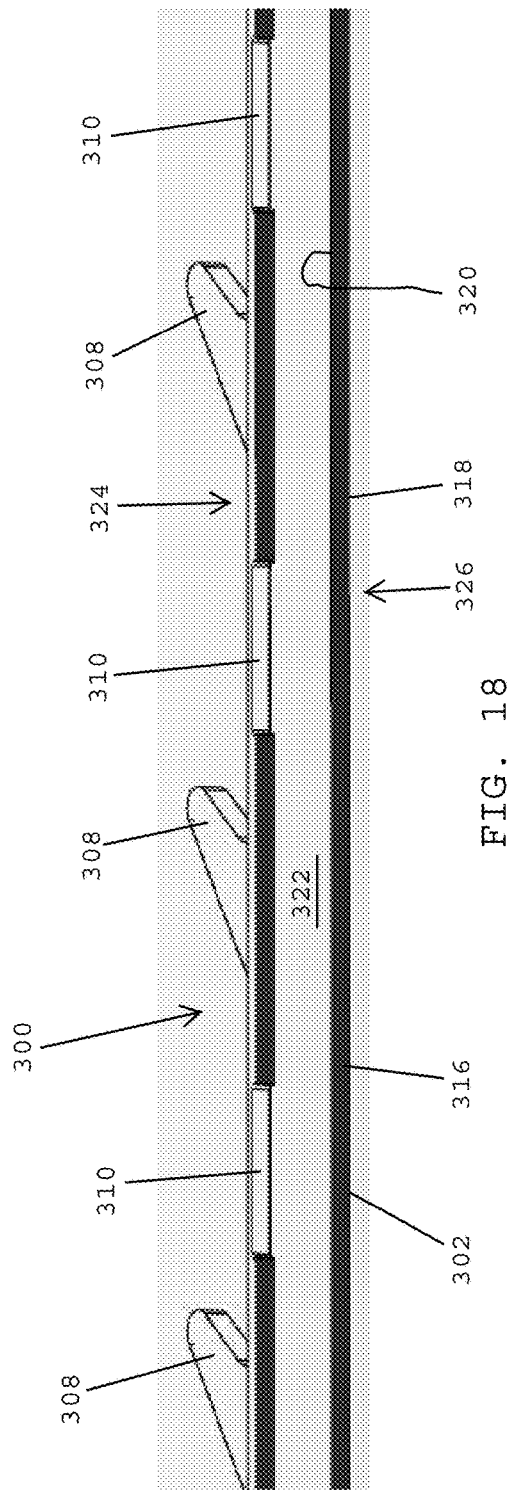
FIG. 18 is a cross-sectional view of the barbed microcatheter shown in FIGS. 17A-17E.

Referring to FIG. 18, in one embodiment, the barbed microcatheter 300 (FIGS. 17A-17E) preferably includes the hollow tube 302 having an outer wall 316 with an outer surface 318 and an inner surface 320 that surrounds the elongated lumen 322 that extends along the length of the hollow tube 302. The barbed microcatheter 300 preferably includes the fluid egress slits 310 that are formed in the topside 324 of the hollow tube 302 and that are spaced from one another along the length of the hollow tube. In one embodiment, fluid (e.g., a therapeutic fluid) flowing through the elongated lumen 322 preferably passes through the fluid egress slits 310 for bathing the tissue surrounding the barbed microcatheter with the fluid. The barbed microcatheter 300 desirably includes the outwardly extending barbs 308 that are spaced from one another along the length of the hollow tube 302. In one embodiment, the barbs 308 may be pairs of symmetric barbs that project from opposite sides of the hollow tube 302.

Figure 19:
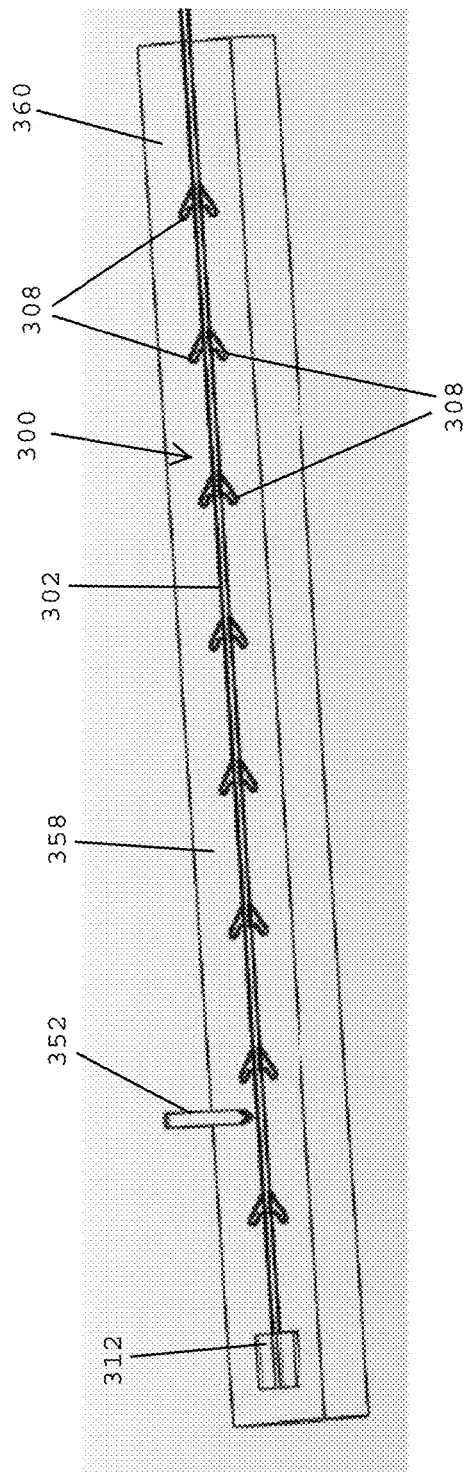
FIG. 19 is a perspective view of a die used for forming spaced fluid egress slits in a top surface of a hollow tube of a barbed microcatheter, in accordance with one embodiment of the present patent application.

Referring to FIG. 19, in one embodiment, a fluid egress slit die 358 and a cutting blade 352 may be utilized for forming the fluid egress slits (FIG. 18) in the topside of the hollow tube 302 of the barbed microcatheter 300. In one embodiment, the fluid egress slit die 358 desirably has a top surface 360 with depressions formed therein, which are adapted to seat undersides of the hollow tube 302, the barbs 308 and the tissue anchor 312 of the barbed microcatheter 300. In one embodiment, after the barbed microcatheter 300 has been positioned atop the die 358, a cutting blade 352 having a sharpened end may be utilized to form the fluid egress slits 310 (FIG. 18) in the topside of the hollow tube 302.

Figure 20A:
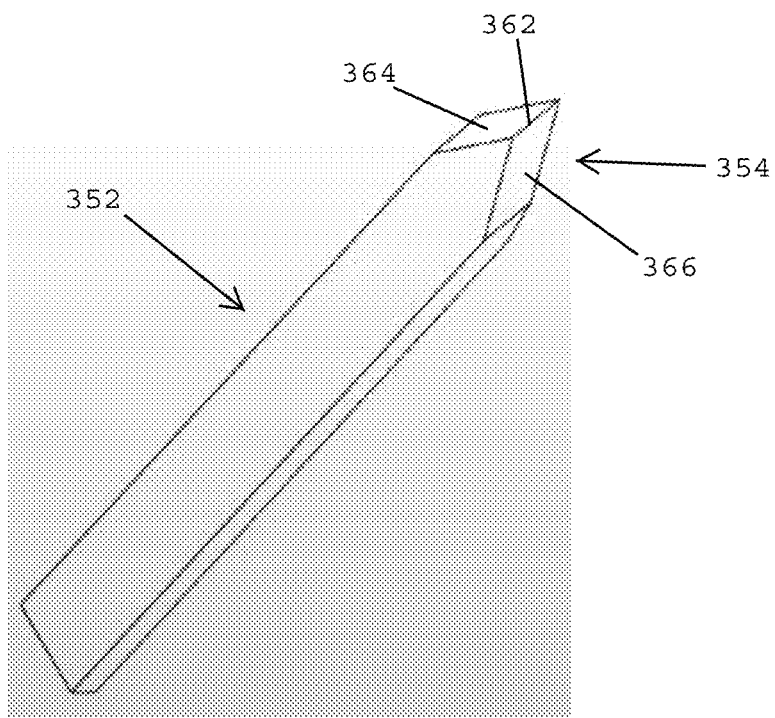
FIG. 20A is a perspective view of a cutting blade used for forming fluid egress slits in a hollow tube of a barbed microcatheter, in accordance with one embodiment of the present patent application.
Figure 20B:
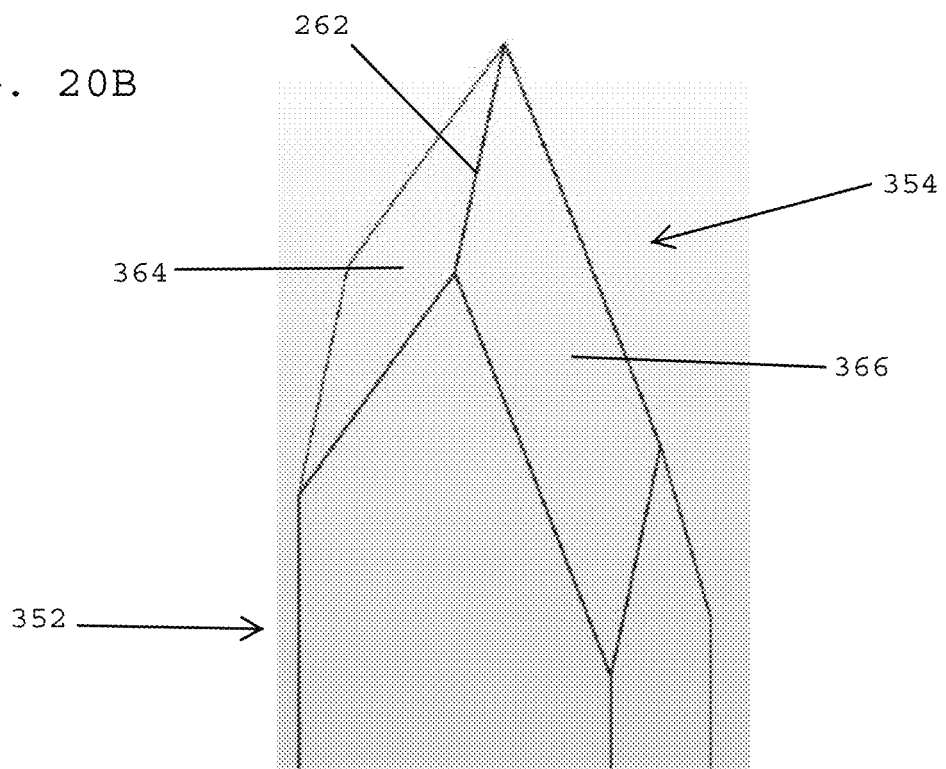
FIG. 20B is a magnified view of a distal end of the cutting blade shown in FIG. 20A.

Referring to FIGS. 20A and 20B, in one embodiment, the cutting blade 352 preferably has a sharpened tip 354 that is utilized to form the fluid egress slits in the outer wall of the hollow tube of the barbed microcatheter. In one embodiment, the sharpened tip 354 has a cutting edge 362 and sloping sidewalls 365, 366 that extend proximally from the cutting edge 362. The exact length of a fluid egress slit that is formed in an outer tube of a barbed microcatheter or a microcatheter blank may be controlled by modifying the extent to which the sharpened tip 354 of the cutting blade 352 is inserted into the hollow tube. In one embodiment, more insertion of the sharpened tip will create a longer fluid egress slit and less insertion of the sharpened tip will create a shorter fluid egress slit.

Figure 21:
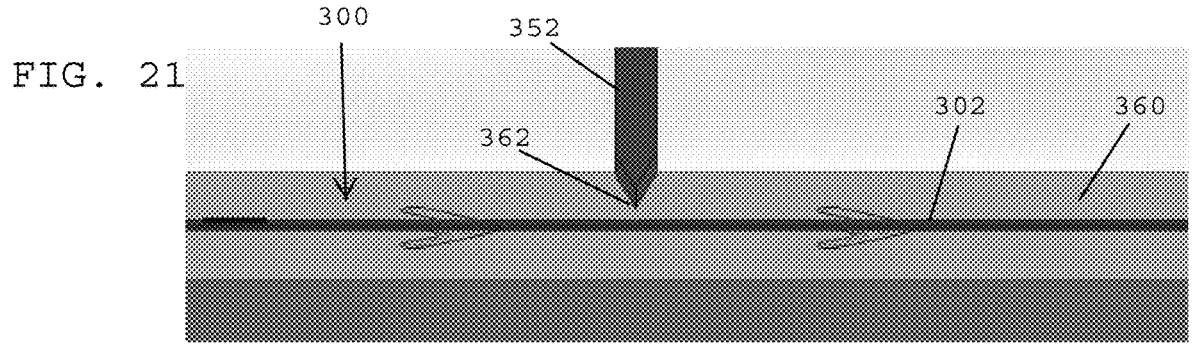
FIG. 21 illustrates a first stage of a method of forming a fluid egress slit in a hollow tube of a barbed microcatheter, in accordance with one embodiment of the present patent application.

Referring to FIG. 21, in one embodiment, after the barbed microcatheter 300 has been positioned within the recesses formed in the top surface 360 of the fluid egress slit die 358, the cutting edge 362 of the cutting blade 352 is preferably juxtaposed with the top side of the hollow tube 302 of the barbed microcatheter 300.

Figure 22:
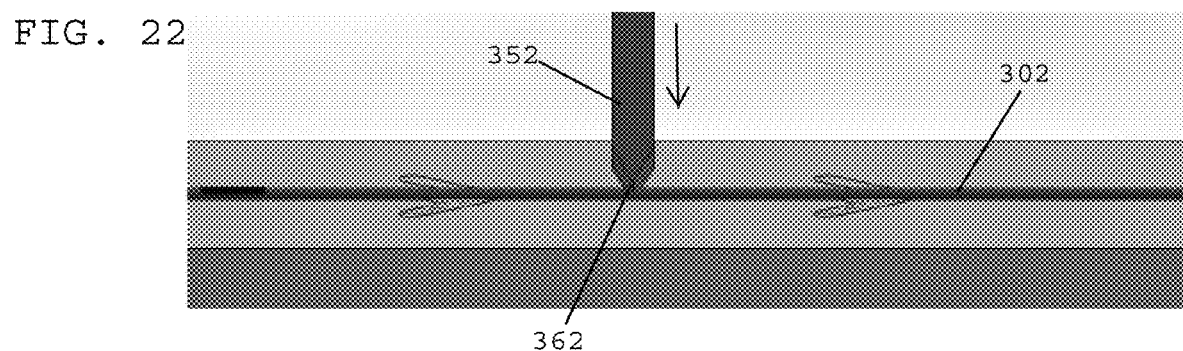
FIG. 22 illustrates a second stage of a method of forming a fluid egress slit in a hollow tube of a barbed microcatheter, in accordance with one embodiment of the present patent application.

Referring to FIG. 22, in one embodiment, the cutting edge 362 at the lower end of the cutting blade 352 is lowered onto the outer surface of the hollow tube 302 for cutting and/or puncturing the outer wall of the hollow tube 302.

Figure 23:
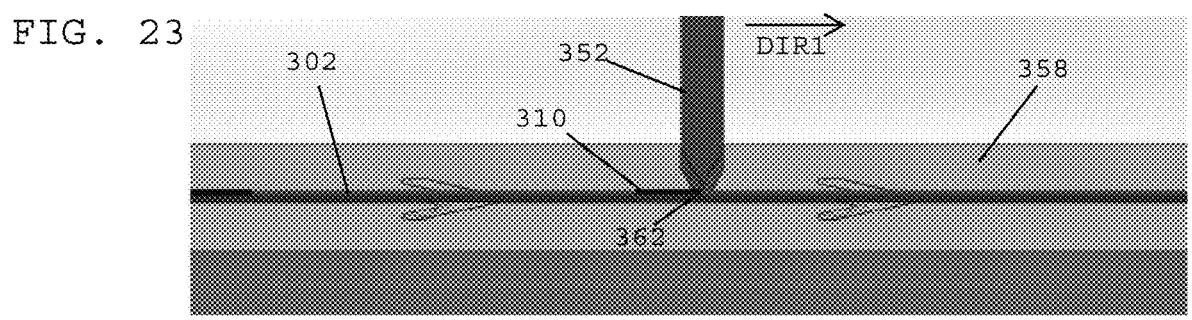
FIG. 23 illustrates a third stage of a method of forming a fluid egress slit in a hollow tube of a barbed microcatheter, in accordance with one embodiment of the present patent application.

Referring to FIG. 23, in one embodiment, with the cutting edge 362 of the cutting blade 352 penetrating the outer wall of the hollow tube 302, the cutting blade 352 is moved in the direction DIR1 relative to the hollow tube 302 and the die 358 for forming the fluid egress slit 310 in the top side of the hollow tube 302. In an alternative embodiment, the cutting blade 352 may remain stationary and the die 358 and barbed microcatheter may be moved relative to the cutting edge 362 of the cutting blade 352 for forming the fluid egress slit 310 in the top side of the hollow tube 302.

Figure 24:
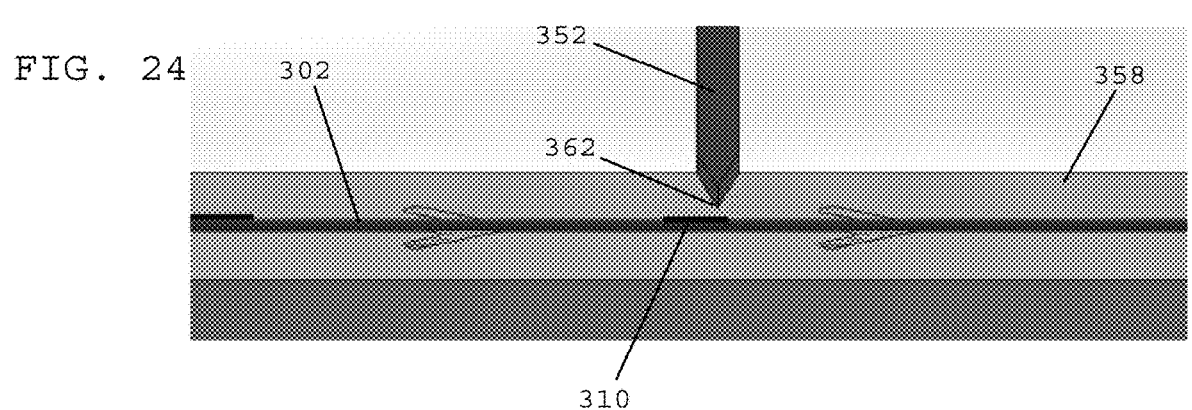
FIG. 24 illustrates a fourth stage of a method of forming a fluid egress slit in a hollow tube of a barbed microcatheter, in accordance with one embodiment of the present patent application.

Referring to FIG. 24, in one embodiment, after the cutting edge 362 of the cutting blade 352 has formed the elongated fluid egress slit 310 in the top side of the hollow tube 302, the cutting blade may be retracted so that the hollow tube 302 and the die 358 may be indexed to the next position for forming another fluid egress slit in the hollow tube. The process may be repeated for forming a plurality of fluid egress slits (e.g., 25 slits, 50 slits, 100 slits) along the length of the hollow tube 302. In one embodiment, the slits may have the same length. In one embodiment, one or more of the fluid egress slits may have different lengths.

Figure 25A:
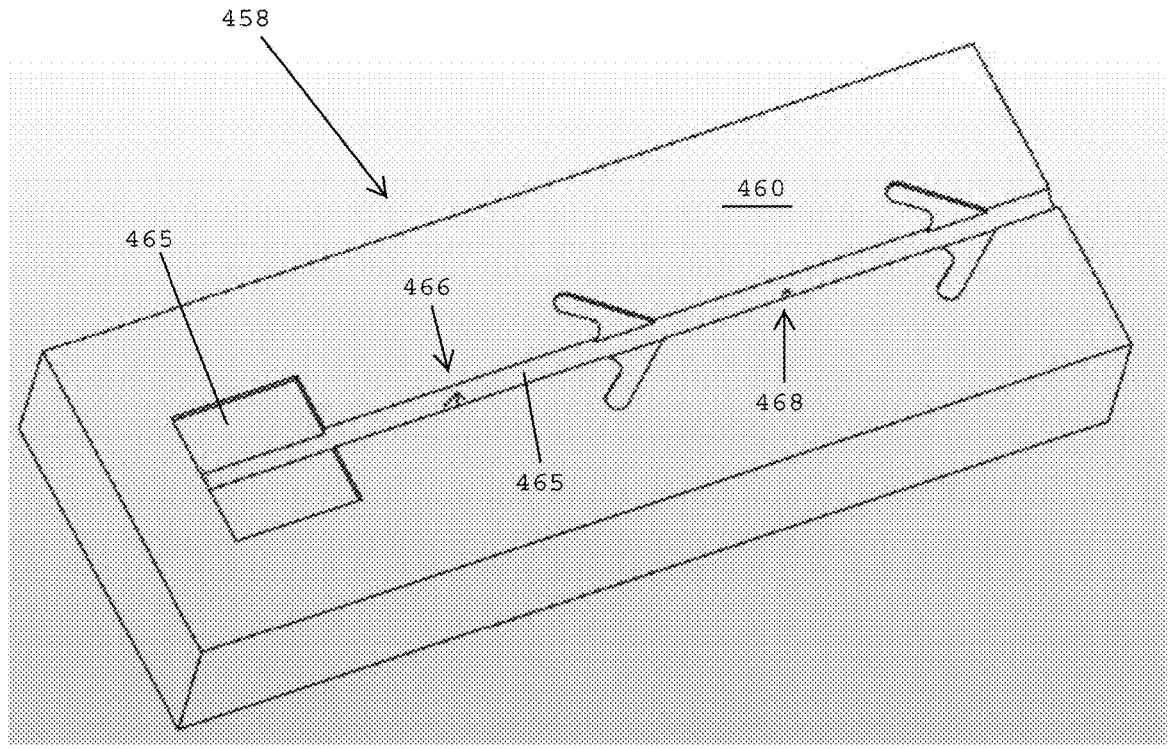
FIG. 25A is a perspective view of a top side of a die used for forming fluid egress slits in a hollow body of a barbed microcatheter, in accordance with one embodiment of the present patent application.
Figure 25B:
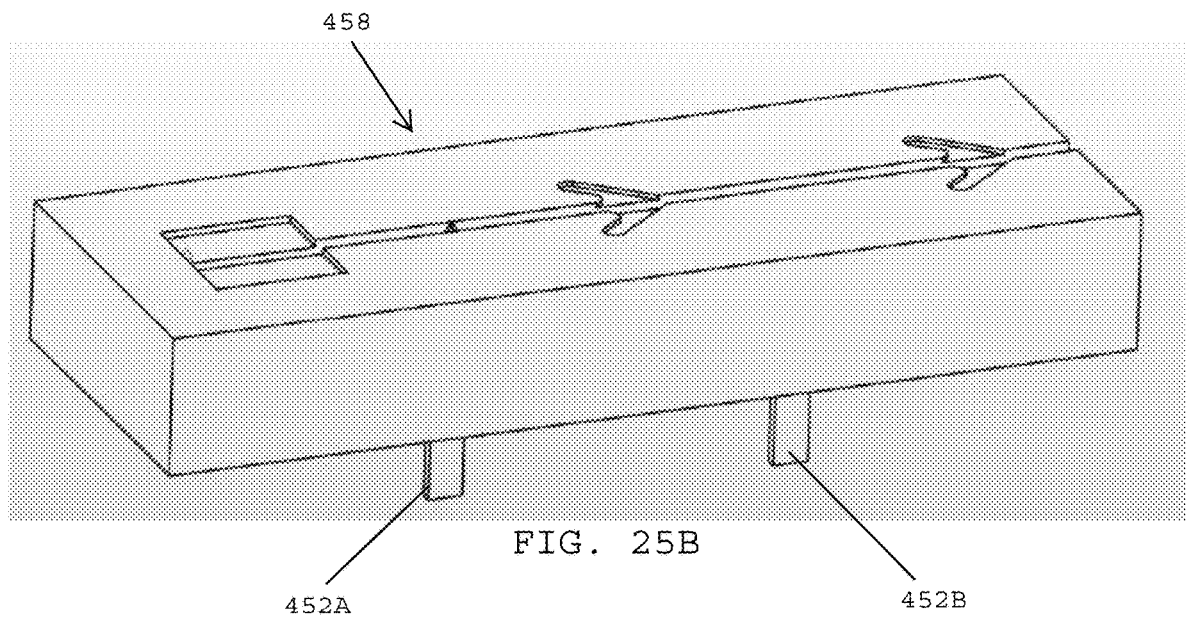
FIG. 25B is another perspective side view of the die shown in FIG. 25A.

Referring to FIGS. 25A-25B, in one embodiment, the fluid egress slits 310 (FIGS. 17A-17E) may be formed in a barbed microcatheter by passing cutting blades 352 (FIG. 20A) through openings provided in a body of a fluid egress slit die 458. In one embodiment, the fluid egress slit die 458 preferably includes a top surface 360 having depressions 365 formed therein that seat a microcatheter blank 128 having barbs cut along the sides (FIG. 9). In one embodiment, the fluid egress slit die 458 desirably includes a first opening 466 configured to receive a first cutting blade 452A and a second opening 468 configured to receive a second cutting blade 452B. In one embodiment, the cutting edges of the respective cutting blades 452A, 452B are advanced into the depression 468 formed in the top face 460 of the die 458 so that the cutting edges are able to engage the outer wall of the hollow tube of a catheter blank for forming fluid egress slits in the outer wall of the hollow tube.

Figure 25C:
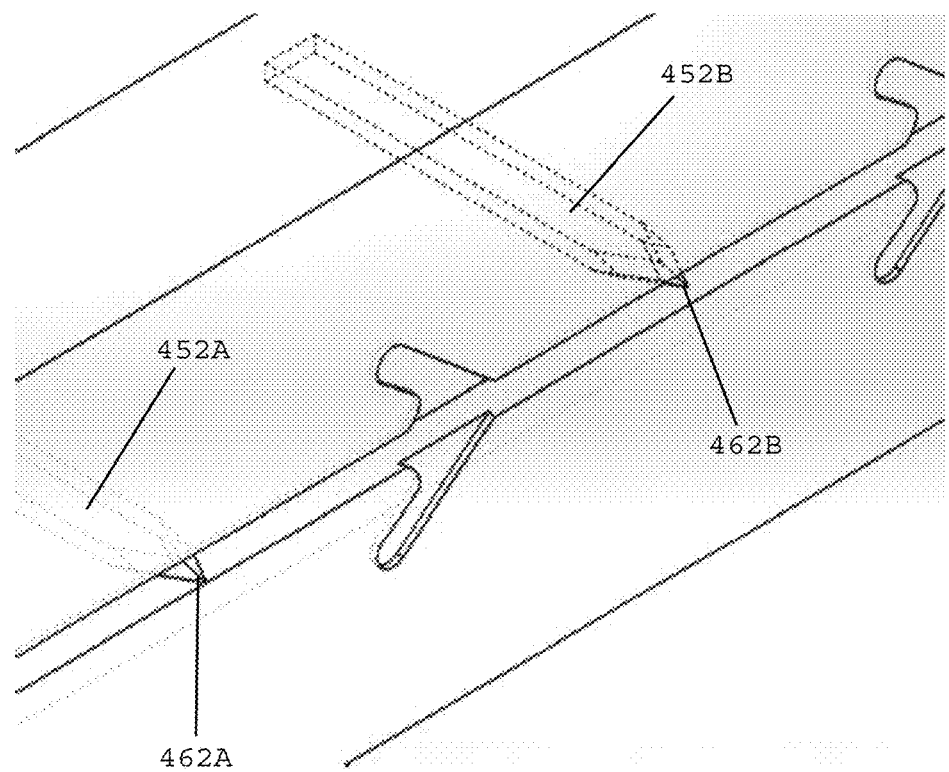
FIG. 25C illustrates a stage of a method of using the die of FIGS. 25A and 25B to form spaced fluid egress slits in a hollow tube of a barbed microcatheter, in accordance with one embodiment of the present patent application.
Figure 25D:
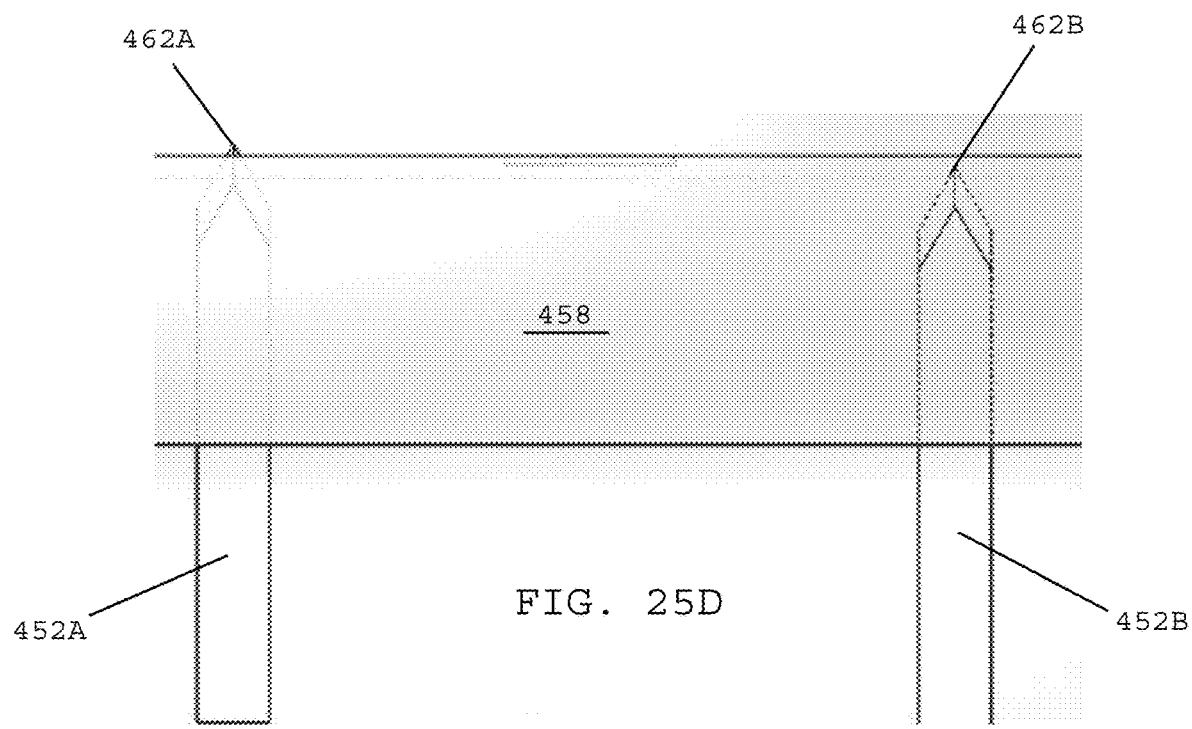
FIG. 25D is a side view of the die shown in FIG. 25C.

Referring to FIGS. 25C and 25D, in one embodiment, the first cutting edge 462A of the first cutting blade 452A is advanced to a greater depth than the second cutting edge 462B of the second cutting blade 452B. As a result, the length of the fluid egress slit formed by the first cutting blade 452A will be greater than the length of the fluid egress slit formed by the second cutting blade 452B.

Figure 26:
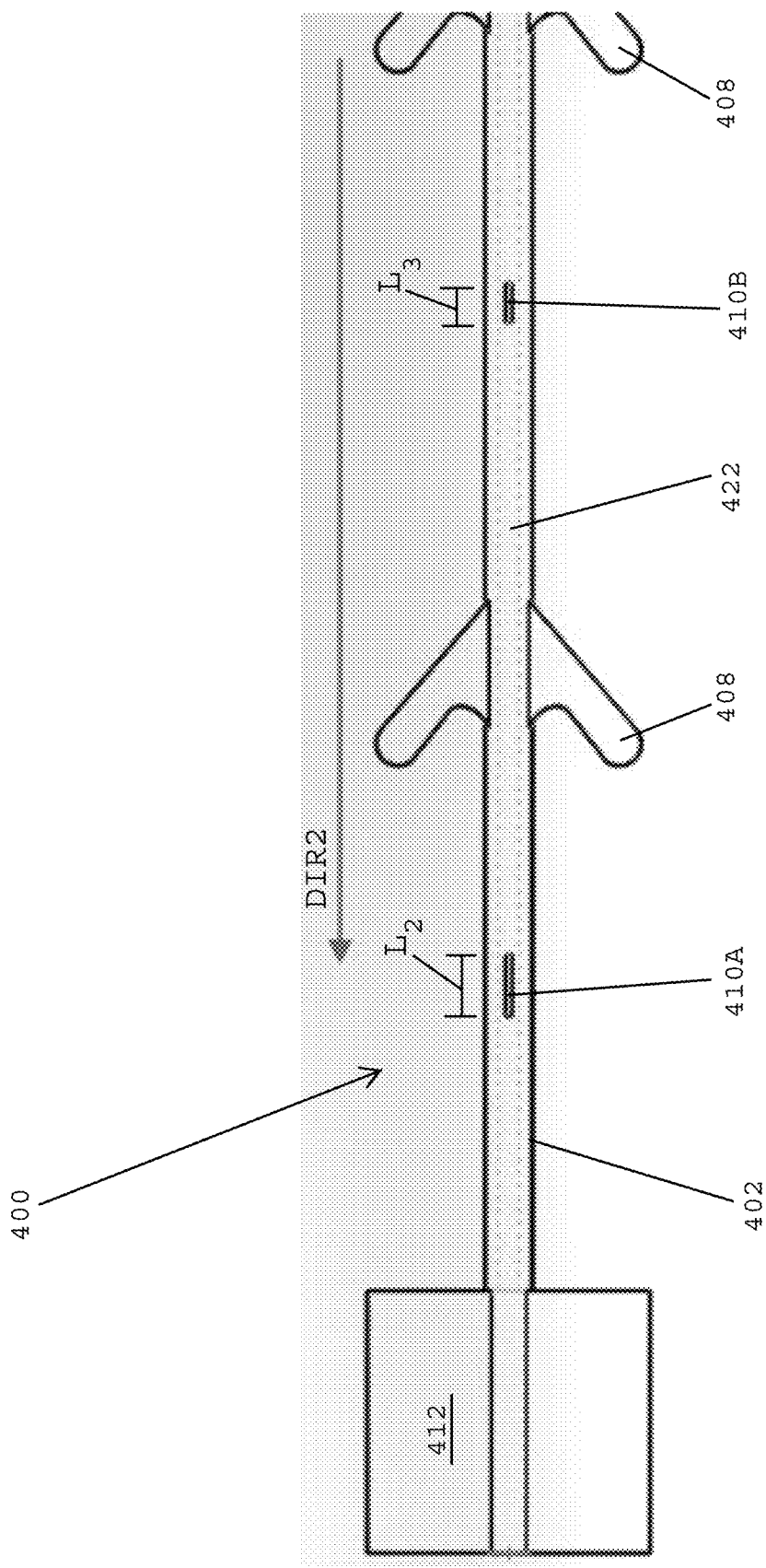
FIG. 26 is a top plan view of a barbed microcatheter including a hollow tube having spaced fluid egress slits formed in a top side of the hollow tube, in accordance with one embodiment of the present patent application.

FIG. 26 shows the barbed microcatheter 400 that is formed utilizing the fluid egress slit die 458 and the cutting blades 452A, 452B shown and described above in FIGS. 25A-25D. In one embodiment, the barbed microcatheter 400 includes a hollow tube 402 with an elongated lumen 422 extending along the length of the hollow tube 402. Barbs 408 project from the sides of the hollow tube 402. An anchor 412 is secured to the proximal end 404 of the hollow tube 402 of the barbed microcatheter 400. The barbed microcatheter includes a first fluid egress slit 410A formed in the outer tube 402 that has a first length $L_2$ that is greater than a second length $L_3$ of a second fluid egress slit 410B that is formed in the outer tube 402. As described above, the respective lengths of the fluid egress slits 410A, 410B may be controlled by the depth of insertion of the cutting edges of the cutting blades 352 (FIGS. 20A and 20B), or by controlling the length of a fluid egress slit that is cut into the hollow tube 402 as the cutting edge of the cutting blade is moved relative to the hollow tube and the fluid egress slit die that seats the hollow tube of the microcatheter blank (e.g., the microcatheter blank 128 shown in FIG. 9).

In one embodiment, a therapeutic fluid flows through the elongated lumen 422 of the hollow tube 402 in the direction DIR2. The therapeutic fluid preferably flows from a fluid source located at a distal end of the hollow tube 402 that is spaced away from the proximal end 404 of the hollow tube. The first fluid egress slit 410A, adjacent the anchor 412, is longer than the second fluid egress slit 410B that is distal to the first fluid egress slit 410A.

Figure 27A:
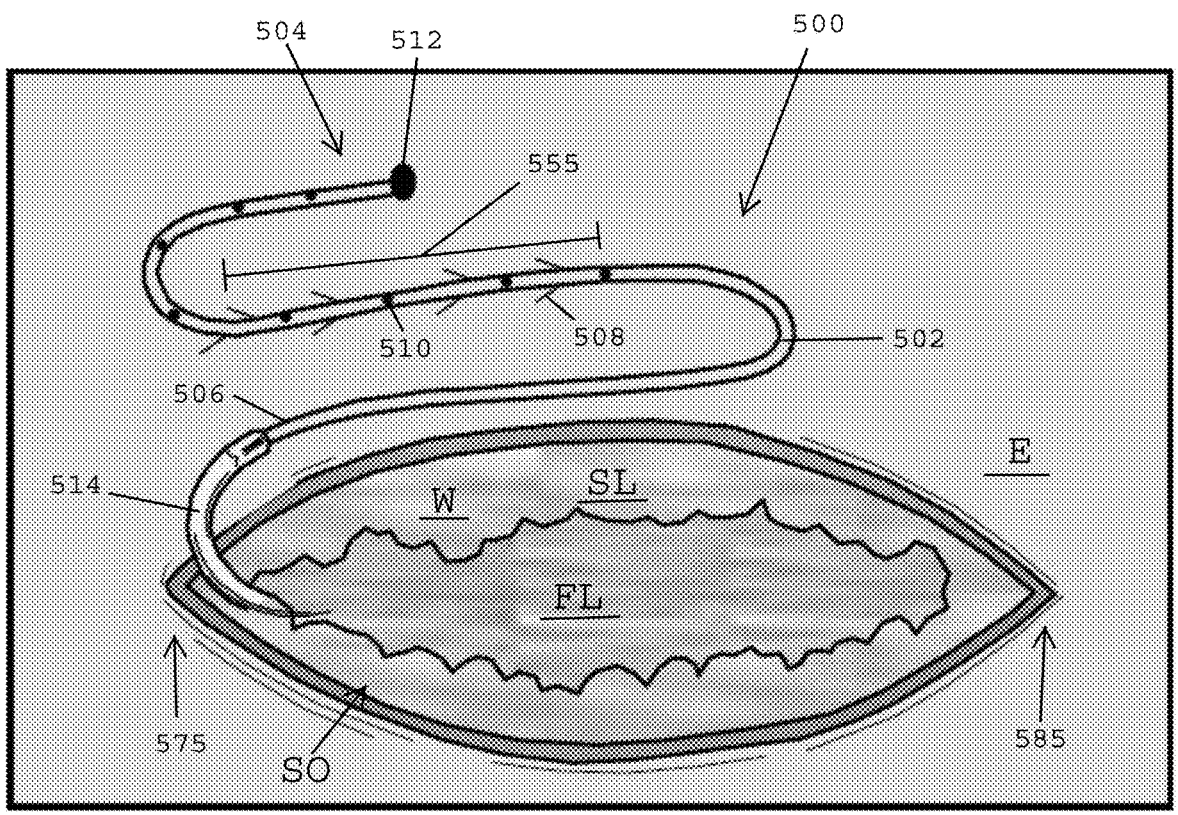
FIG. 27A illustrates a first stage of a method of using a barbed microcatheter for infusing therapeutic fluid into a wound, in accordance with one embodiment of the present patent application.

Referring to FIG. 27A, in one embodiment, a barbed microcatheter 500 is preferably used for infusing a therapeutic fluid into the tissue of a patient, such as into a wound of the patient. In one embodiment, the barbed microcatheter 500 preferably includes a hollow tube 502 having a first end 504 and a second end 506. The barbed microcatheter 500 desirably includes barbs 508 that are spaced from one another along the length of the hollow tube 502 and that project from opposite sides of the hollow tube. In one embodiment, the barbed microcatheter includes a plurality of fluid egress openings 510 that are formed in the outer wall of the hollow tube 502, and that are spaced from one another along the length of the hollow tube. In one embodiment, the hollow tube 502 has an elongated lumen (e.g., elongated lumen 122 shown in FIG. 3) that extends along the length of the hollow tube and that is adapted to receive the therapeutic fluid that is infused into the tissue of the patient. The fluid egress openings 510 are preferably in fluid communication with the elongated lumen so that fluid flowing through the elongated lumen of the hollow tube may pass out of the hollow tube via the fluid egress openings 510. In one embodiment, the barbed microcatheter 500 may included a tissue anchor 512 that is secured to the first end 504 of the hollow tube 502, and a surgical needle 514 that is secured to the second end 506 of the hollow tube 502.

In one embodiment, the epidermis E of a patient has a surgical opening SO formed therein to define a wound W having wound tissue including a subcutaneous layer SL and a fascia layer FL. The wound has a first end 575 and a second end 585 that is spaced from the first end 575.

In one embodiment, the barbed microcatheter 500 preferably includes an intermediate section 555 that contains at least some of the fluid egress openings 510 and the barbs 508. In one embodiment, the barbs 508 in the intermediate section 555 of the barbed microcatheter 500 preferably bite into the tissue within the wound W for anchoring the barbed microcatheter in place within the wound W. In one embodiment, the second end 506 of the hollow tube 502 is preferably devoid of fluid egress openings. In one embodiment, the second end 506 of the hollow tube 502 is preferably passed outside of the patient so that the needle 514 may be detached from the second end of the hollow tube, whereupon, a therapeutic fluid may be directed into the second end of the hollow tube.

Figure 27B:
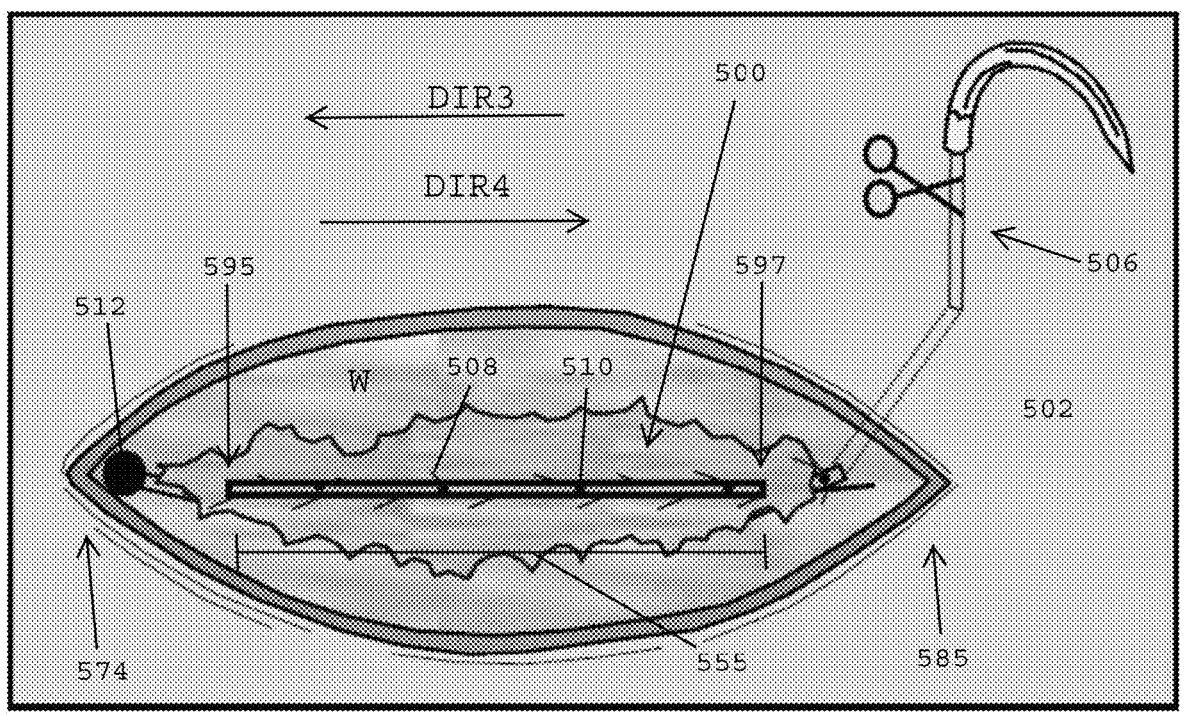
FIG. 27B illustrates a second stage of a method of using a barbed microcatheter for infusing therapeutic fluid into a wound, in accordance with one embodiment of the present patent application.

Referring to FIGS. 27A and 27B, in one embodiment, a method of delivering a therapeutic fluid to tissue desirably includes positioning the barbed microcatheter 500 adjacent the first end 575 of the wound W. In one embodiment, the needle 514 is used to form a first tissue opening 595 at the first end 575 of the wound, and the hollow tube 502 is pulled completely through the first tissue opening 595 until the tissue anchor 512 abuts against tissue at the first end of the wound W.

In one embodiment, the needle 514 is used to form a second tissue opening 597 at the second end 585 of the wound W and the hollow tube 502 is pulled completely through the second tissue opening 597 so that the barbs 508 projecting outwardly from opposite sides of the hollow tube 502 engage tissue within the wound W that is located between the first and second ends 575, 585 of the wound W.

In one embodiment, the needle 514 is passed through the epidermis later E of the patient so that the needle 514 and the second end 506 of the hollow tube 502 are located outside the patient.

Referring to FIG. 27B, in one embodiment, after the barbed microcatheter 500 has been implanted in the wound W, the intermediate section 555 of the hollow tube 502 that contains barbs 508 and fluid egress openings 510 may extend along a linear path between the first and second ends 575, 585 of the wound W. The barbs 508 preferably bite into the tissue within the wound W to prevent the hollow tube 502 from slipping or moving in the direction designated DIR3. The tissue anchor 512 preferably engages the tissue at the first end 575 of the wound W to prevent the hollow tube 502 from slipping or moving in the direction designated DIR4.

In one embodiment, the second end 506 of the hollow tube 502 is cut for detaching the needle 514 from the hollow tube 502 and for providing access to the elongated lumen that extends through the hollow tube 502.

Figure 27C:
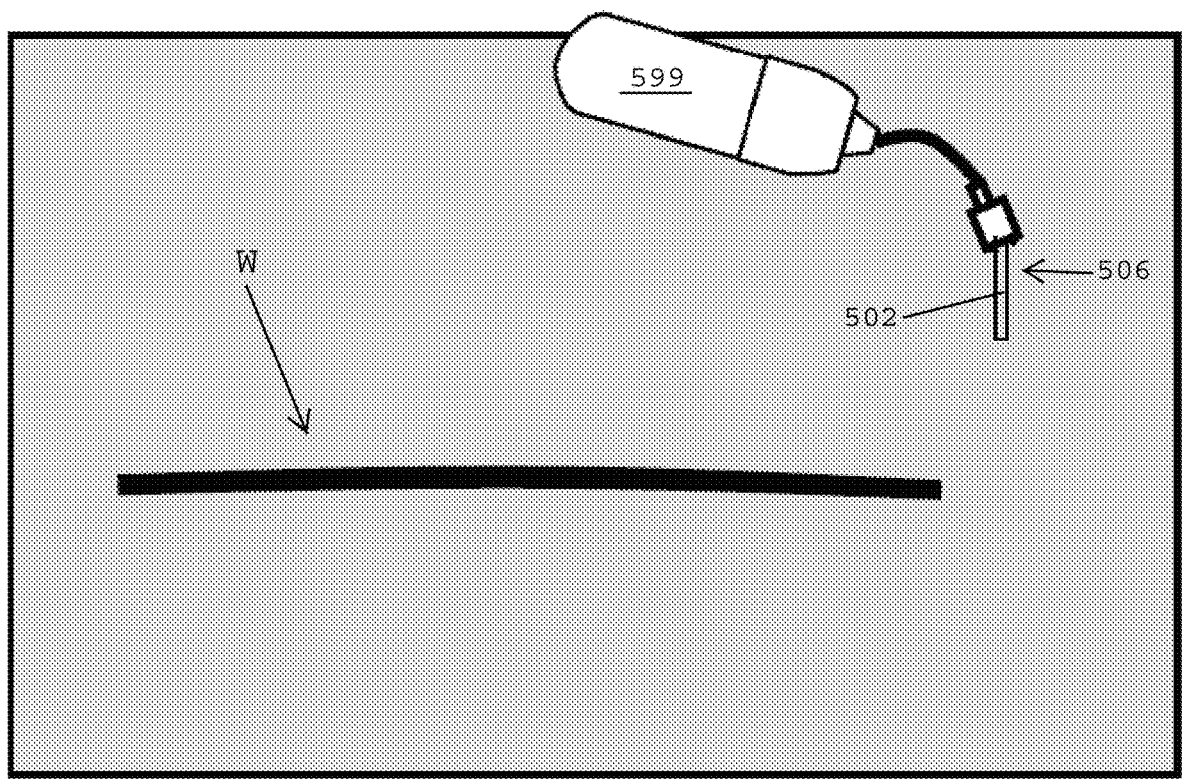
FIG. 27C illustrates a third stage of a method of using a barbed microcatheter for infusing therapeutic fluid into a wound, in accordance with one embodiment of the present patent application.

Referring to FIG. 27C, in one embodiment, the wound W may be closed such as by using sutures, staples, tissue fasteners and tissue adhesive. A container 599 holding a therapeutic fluid may be coupled with the cut second end 506 of the hollow tube 502 that extends outside the patient for introducing the therapeutic fluid into the hollow tube 502. The therapeutic fluid preferably flows into the elongated lumen of the hollow tube and passes through the fluid egress openings 510 (FIG. 27B) for infusing the wound W with the therapeutic fluid.

Figure 28A:
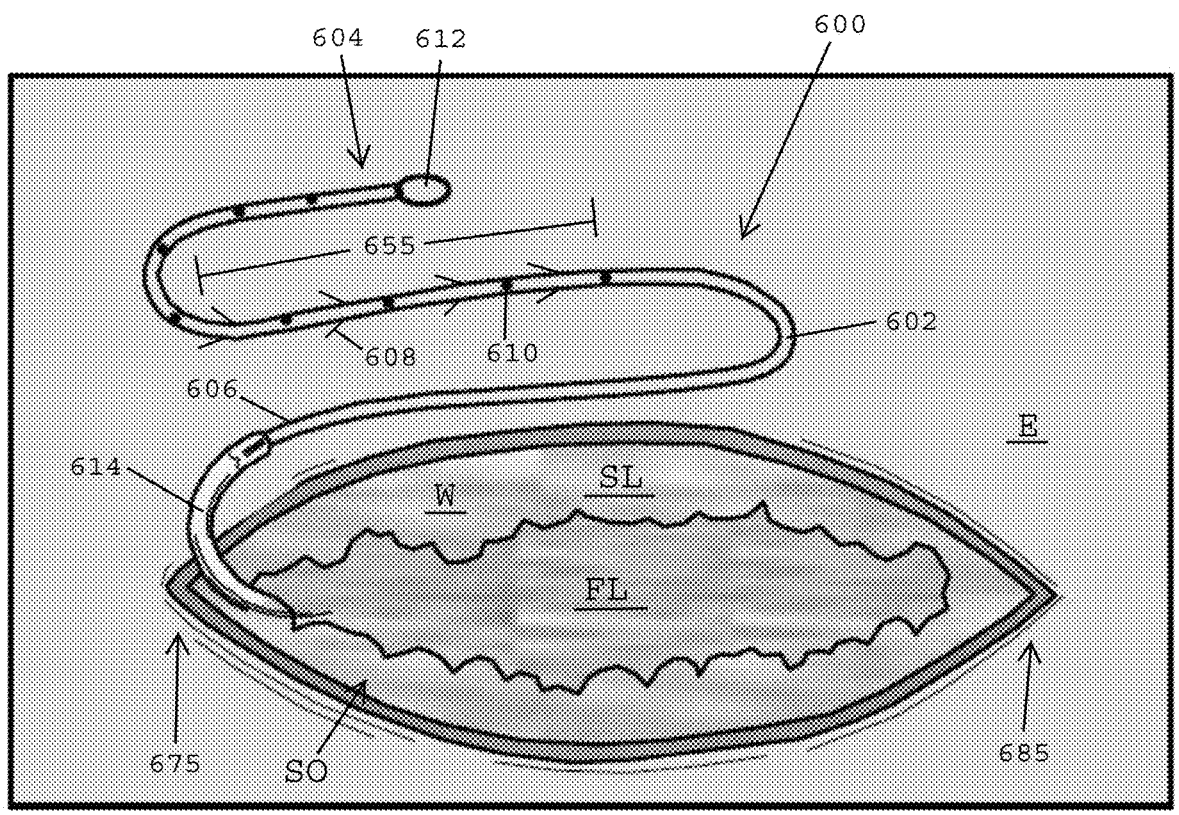
FIG. 28A illustrates a first stage of a method of using a barbed microcatheter having a non-linear configuration for infusing therapeutic fluid into a wound, in accordance with one embodiment of the present patent application.

Referring to FIG. 28A, in one embodiment, a barbed microcatheter 600 is preferably used for infusing a therapeutic fluid into the tissue of a patient, such as into a wound of the patient. In one embodiment, the barbed microcatheter 600 preferably includes a hollow tube 602 having a first end 604 and a second end 606. The barbed microcatheter 600 desirably includes barbs 608 that are spaced from one another along the length of the hollow tube 602 and that project from opposite sides of the hollow tube. In one embodiment, the barbed microcatheter includes a plurality of fluid egress openings 610 that are formed in the outer wall of the hollow tube 602, and that are spaced from one another along the length of the hollow tube. In one embodiment, the hollow tube 602 has an elongated lumen (e.g., elongated lumen 122 shown in FIG. 3) that extends along the length of the hollow tube and that is adapted to receive the therapeutic fluid that is infused into the tissue of the patient. The fluid egress openings 610 are preferably in fluid communication with the elongated lumen so that fluid flowing through the elongated lumen of the hollow tube may pass out of the hollow tube via the fluid egress openings 610. In one embodiment, the barbed microcatheter 600 may included a tissue anchor 612 that is secured to the first end 604 of the hollow tube 602, and a surgical needle 614 that is secured to the second end 606 of the hollow tube 602.

In one embodiment, the epidermis E of a patient has a surgical opening SO formed therein to define a wound W having wound tissue including a subcutaneous layer SL and a fascia layer FL. The wound has a first end 675 and a second end 685 that is spaced from the first end 675.

In one embodiment, the barbed microcatheter 600 preferably includes an intermediate section 655 that contains at least some of the fluid egress openings 610 and at least some of the barbs 608. In one embodiment, the barbs 608 in the intermediate section 655 of the barbed microcatheter 600 preferably bite into the tissue within the wound W for anchoring the barbed microcatheter in place within the wound W. In one embodiment, the second end 606 of the hollow tube 602 is preferably devoid of fluid egress openings. In one embodiment, the second end 606 of the hollow tube 602 is preferably passed outside of the patient so that the needle 614 may be detached from the second end of the hollow tube, whereupon, a therapeutic fluid may be directed into the second end of the hollow tube.

Figure 28B:
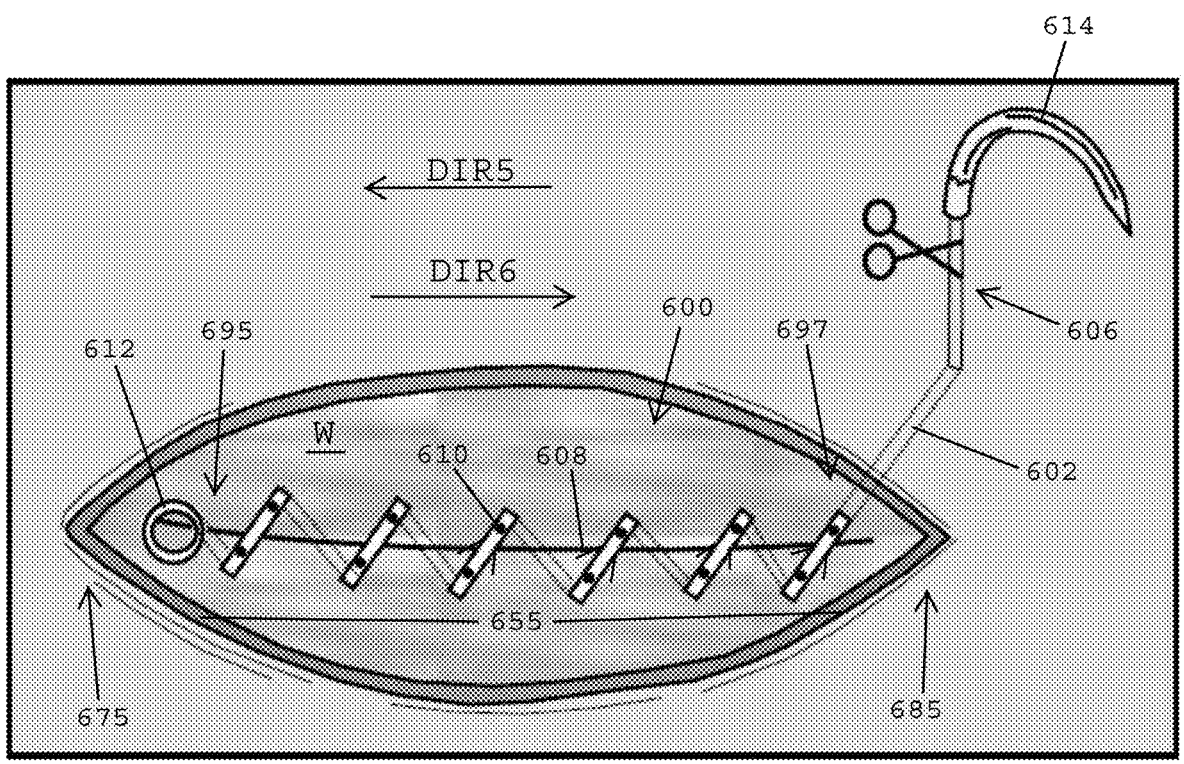
FIG. 28B illustrates a second stage of a method of using a barbed microcatheter having a non-linear configuration for infusing therapeutic fluid into a wound, in accordance with one embodiment of the present patent application.

Referring to FIGS. 28A and 28B, in one embodiment, a method of delivering a therapeutic fluid to tissue desirably includes positioning the barbed microcatheter 600 adjacent the first end 675 of the wound W. In one embodiment, the needle 614 is used to form a first tissue opening 695 at the first end 675 of the wound, and the hollow tube 602 is pulled completely through the first tissue opening 695 until the tissue anchor 612 abuts against tissue at the first end of the wound W. The needle 614 is used to make additional bites into the tissue so that the hollow tube 602 follows a non-linear path between the first and second ends 675, 685 of the wound W.

In one embodiment, the needle 614 is used to form a final tissue opening 697 at the second end 685 of the wound W and the hollow tube 602 is pulled completely through the second tissue opening 697 so that the barbs 608 projecting outwardly from opposite sides of the non-linearly configured hollow tube 602 engage tissue within the wound W that is located between the first and second ends 675, 685 of the wound W.

In one embodiment, the needle 614 is passed through the epidermis later E of the patient so that the needle 614 and the second end 606 of the hollow tube 602 are located outside the patient.

Referring to FIG. 28B, in one embodiment, after the barbed microcatheter 600 has been implanted in the wound W, the intermediate section 655 of the hollow tube 602 that contains barbs 608 and fluid egress openings 610 may extend along a non-linear path between the first and second ends 675, 685 of the wound W. The barbs 608 preferably bite into the tissue within the wound W to prevent the hollow tube 602 from slipping or moving in the direction designated DIR5. The tissue anchor 612 preferably engages the tissue at the first end 675 of the wound W to prevent the hollow tube 602 from slipping or moving in the direction designated DIRE.

In one embodiment, the second end 606 of the hollow tube 602 is cut for detaching the needle 614 from the hollow tube 602 and for providing access to the elongated lumen that extends through the hollow tube 602.

Figure 28C:
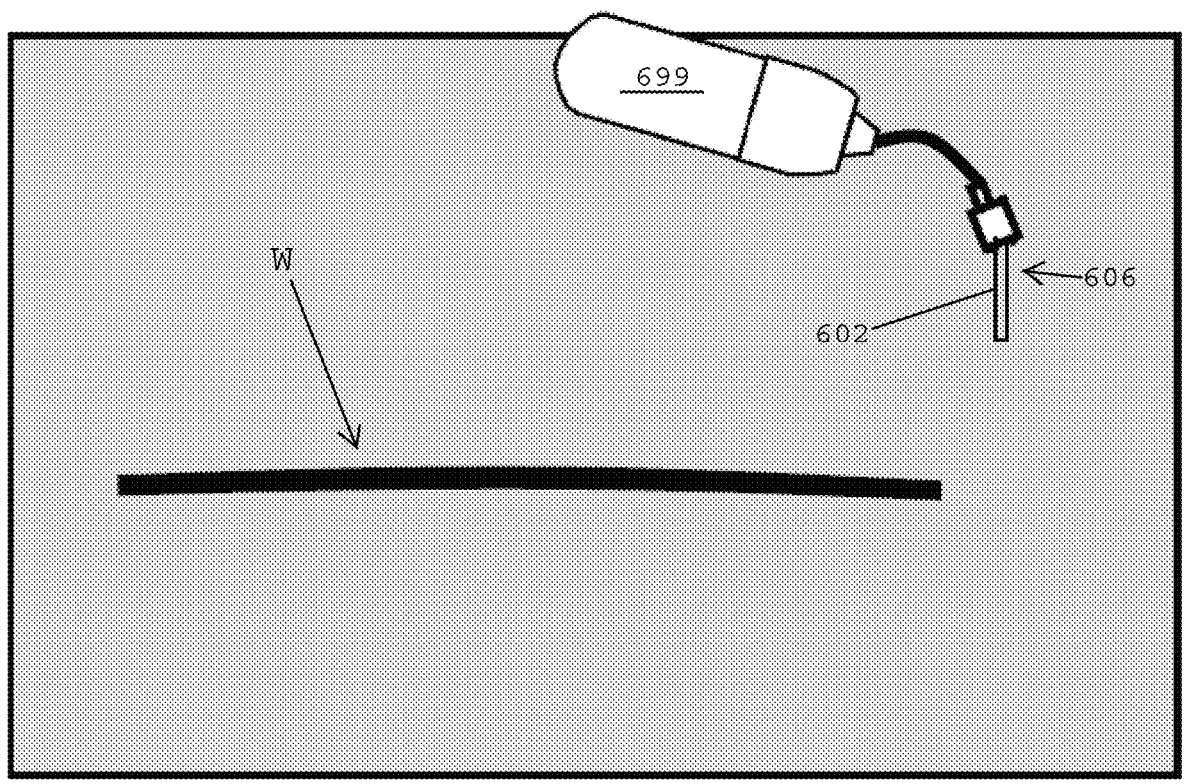
FIG. 28C illustrates a third stage of a method of using a barbed microcatheter having a non-linear configuration for infusing therapeutic fluid into a wound, in accordance with one embodiment of the present patent application.

Referring to FIG. 28C, in one embodiment, the wound W may be closed such as by using sutures, staples, tissue fasteners and tissue adhesive. A container 699 holding a therapeutic fluid may be coupled with the cut second end 606 of the hollow tube 602 that extends outside the patient for introducing the therapeutic fluid into the hollow tube 602. The therapeutic fluid preferably flows into the elongated lumen of the hollow tube and passes through the fluid egress openings 610 (FIG. 28B) for infusing the wound W with the therapeutic fluid.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of making a barbed microcatheter having fluid egress openings comprising:
   compressing first and second lateral sides of a polymer blank to form a barbed microcatheter blank including a first flattened region extending along a first lateral side of said barbed microcatheter blank, a second flattened region extending along a second lateral side of said barbed microcatheter blank, and a hollow tube with an elongated lumen located between said first and second flattened regions;
   removing material from said first and second flattened regions of said barbed microcatheter blank to form barbs that project outwardly from opposite sides of said hollow tube;
   forming fluid egress openings in a wall of said hollow tube that are in fluid communication with the elongated lumen of said hollow tube.

2. The method as claimed in claim 1, further comprising:
   compressing a proximal end of said polymer blank to form a tissue anchor connected with a proximal end of said hollow tube; and
   securing a needle to a distal end of said hollow tube.

3. The method as claimed in claim 1, further comprising using at least one cutting element for forming said fluid egress openings in said wall of said hollow tube.

4. The method as claimed in claim 3, wherein the forming fluid egress openings step comprises:
   forming a first fluid egress opening in said wall of said hollow tube having a first size;
   forming a second fluid egress opening is said wall of said hollow tube having a second size that is larger than the first size of said first fluid egress opening.

5. The method as claimed in claim 3, wherein the forming fluid egress openings step comprises forming a series of progressively larger fluid egress openings in said wall of said hollow tube.

6. The method as claimed in claim 1, wherein said fluid egress openings are formed simultaneously during the forming fluid egress openings step.

7. The method as claimed in claim 1, wherein said fluid egress openings are formed independently of one another and at different times during the forming fluid egress openings step.

8. The method as claimed in claim 3, wherein said at least one cutting element comprises cutting elements selected from the group consisting of needles, needles having tapered tips, and cutting blades.

9. The method as claimed in claim 2, wherein said tissue anchor connected with the proximal end of said hollow tube comprises a flattened tab having a length and a width.

10. The method as claimed in claim 1, wherein the compressing first and second lateral sides of said polymer blank step comprises:
    placing said polymer blank into a pressing die having an upper pressing die part overlying said polymer blank and a lower pressing die part that opposes said upper pressing die part and that is located under said polymer blank;
    moving said pressing die into a closed position for compressing upper and lower surfaces of the first and second lateral sides of said polymer blank for forming said first and second flattened regions and said hollow tube.

11. The method as claimed in claim 10, wherein said upper pressing die part comprises a plurality of cutting elements projecting from an underside of said upper pressing die part, wherein when said pressing die is in the closed position, said cutting elements engage said hollow tube for forming said fluid egress openings in said hollow tube.

12. The method as claimed in claim 1, wherein the removing material step comprises cutting said first and second flattened regions of said barbed microcatheter blank to form said barbs that project outwardly from the opposite sides of said hollow tube.

13. The method as claimed in claim 12, wherein the cutting step comprises:
    placing said barbed microcatheter blank including said first and second flattened regions and said hollow tube into a cutting die having an upper cutting die part and a lower cutting die part that opposes said upper cutting die part;
    moving said cutting die into a closed position for cutting said first and second flattened regions of said barbed microcatheter blank for forming said barbs that project outwardly from the opposite sides of said hollow tube.

14. The method as claimed in claim 13, wherein said upper cutting die part comprises a plurality of cutting elements projecting from an underside of said upper cutting die part, wherein when said cutting die is in the closed position said cutting elements engage said hollow tube for forming said fluid egress openings in said hollow tube.

15. The method as claimed in claim 1, wherein the compressing first and second lateral sides of said polymer blank step comprises using pressing rollers for compressing upper and lower surfaces of the first and second lateral sides of said polymer blank for forming said first and second flattened regions and said hollow tube of said barbed microcatheter blank.

16. A method of making a barbed microcatheter having fluid egress openings comprising:
    obtaining a barbed microcatheter blank including a hollow tube having a proximal end, a distal end, and an elongated lumen that extends between the proximal and distal ends of said hollow tube, and first and second flattened regions that extend along opposite sides of said hollow tube;
    removing material from said first and second flattened regions of said barbed microcatheter blank to form barbs projecting outwardly from the opposite sides of said hollow tube;
    using one or more cutting elements for forming fluid egress openings in a wall of said hollow tube that are in fluid communication with the elongated lumen of said hollow tube;
    forming a tissue anchor that is connected with the proximal end of said hollow tube;
    securing a surgical needle with the distal end of said hollow tube.

* * * * *